United States Patent
Schryver et al.

(10) Patent No.: US 10,588,989 B2
(45) Date of Patent: Mar. 17, 2020

(54) SANITIZED ANIMAL BEDDING MATERIAL AND PROCESS

(71) Applicant: Green Products Company, Conrad, IA (US)

(72) Inventors: Mathew Schryver, Marshalltown, IA (US); Aubrey F. Mendonca, Ames, IA (US)

(73) Assignee: Green Products Company, Conrad, IA (US)

( * ) Notice: Subject to any disclaimer, the term of this patent is extended or adjusted under 35 U.S.C. 154(b) by 811 days.

(21) Appl. No.: 14/824,719

(22) Filed: Aug. 12, 2015

(65) Prior Publication Data

US 2016/0074543 A1 Mar. 17, 2016

Related U.S. Application Data

(62) Division of application No. 14/487,316, filed on Sep. 16, 2014, now Pat. No. 9,144,616.

(51) Int. Cl.
*A61L 2/04* (2006.01)
*A01K 1/015* (2006.01)

(52) U.S. Cl.
CPC .............. *A61L 2/04* (2013.01); *A01K 1/0152* (2013.01); *A01K 1/0155* (2013.01)

(58) Field of Classification Search
CPC ................................ A61L 2/04; A01K 1/0155
See application file for complete search history.

(56) References Cited

U.S. PATENT DOCUMENTS

| | | | |
|---|---|---|---|
| 3,256,857 A | 6/1966 | Karras |
| 4,108,601 A | 8/1978 | Wolff |
| 4,166,096 A | 8/1979 | Gillis et al. |
| 4,238,447 A | 12/1980 | Wolff |
| 4,284,600 A | 8/1981 | Gillis et al. |
| 4,759,909 A | 7/1988 | Joslyn |
| 5,429,800 A | 7/1995 | Miraldi et al. |
| 2003/0192485 A1 | 10/2003 | Opfel |
| 2011/0083200 A1 | 4/2011 | Jung et al. |

(Continued)

FOREIGN PATENT DOCUMENTS

| | | |
|---|---|---|
| CN | 101487000 A | 7/2009 |
| CN | 101492700 A | 7/2009 |
| CN | 101638641 A | 2/2010 |

(Continued)

OTHER PUBLICATIONS

English Translation of Document No. CN 102796672 (A) provided by the European Patent Office Espacenet.com: Verticillium lecanii solid fermentation medium, preparation method and application; Nov. 28, 2012.*

(Continued)

*Primary Examiner* — Kevin Joyner
(74) *Attorney, Agent, or Firm* — McKee, Voorhees & Sease, PLC

(57) ABSTRACT

The present invention provides compositions and methods for sanitization or sterilization of, or reduction or elimination of microbes from, PFR material, in particular material for use as an animal bedding. In another aspect, the invention provides sanitized or sterilized material, and especially animal bedding material, prepared using the described compositions and methods.

21 Claims, 11 Drawing Sheets

(56) References Cited

U.S. PATENT DOCUMENTS

2012/0034289 A1* 2/2012 De Leij ............... A01K 1/0152
424/409
2013/0220228 A1 8/2013 Theis et al.

FOREIGN PATENT DOCUMENTS

| CN | 102796672 A | 11/2012 |
|----|-------------|---------|
| EP | 2647694 A2 | 10/2013 |
| WO | 2013019916 | 2/2013 |
| WO | 2013019916 A2 | 2/2013 |

OTHER PUBLICATIONS

CN101487000—English.
CN101492700—English.
CN101638641—English.
CN102796672—English.
Leya, L, Mikusa, S., et al., "Effect of Corncob bedding with Aspen Chip Bedding on Rat EEG and Pain Models", AALAS Poster, 1 page. Dec. 31, 2011.
Krohn, TC, and Hansen, AK, "Evaluation of corncob as Bedding for Rodents", Scand. J. Lab. Animal Sci. 35, 1 page. Dec. 31, 2008.
"Technical info on PJ Murphy Sani chips", 7090A Aspen Sani Chips, 1 page, retrieved from the internet on Aug. 31, 2014.
Domer, DA, Erickson, RL, et al., "The Impact of Bedding Type on Cage Change out Frequency", 1 page. Dec. 31, 2011.
Horn MJ, Williams SV, et al., "The Impacts of Cage Density, Sanitation Frequency, and Bedding Type on Selected Measures of Animal Wellbeing, Health, and Cage Environment", AALAS Scientific Session, 1 page. Dec. 31, 2010.
Ghosh, Sonali, "Superdormant Spores of *Bacillus* Species Have Elevated Wet-Heat Resistance and Temperature Requirements for Heat Activation", Journal of Bacteriology, vol. 191, No. 18, published Jul. 10, 2009.

\* cited by examiner

SANITIZED ANIMAL BEDDING MATERIAL AND PROCESS

CROSS-REFERENCE TO RELATED APPLICATIONS

This is a Divisional Application of U.S. Ser. No. 14/487,316 filed Sep. 16, 2014, which is herein incorporated by reference in its entirety.

FIELD OF THE INVENTION

The present invention relates generally to the fields of microbial physiology, specifically relating to microbiology, and to materials for bedding used in the environment of contained animals.

BACKGROUND OF THE INVENTION

Corncob particles that are not sterilized or sanitized (hereinafter referred to as traditional corncob) and used as animal bedding worldwide have relatively high microbial populations. High levels of microbial contamination increase the likelihood that disease-causing microorganisms (pathogens) may be present. Pathogens in bedding materials can be harmful to animals by infection of wounds or by causing digestive or respiratory problems and thereby confounding results of experiments. Consequently, many animal research facilities control against pathogens in their animal bedding by either purchasing bedding that has been irradiated or autoclaving bedding that has not been irradiated.

In the field of animal management, specifically that of laboratory animals, such as rodents, all environmental conditions to which the animals are exposed must be tightly controlled to prevent contaminations of the animals by the external environment and/or nosocomial contamination.

Research animals are becoming more valuable because many disease models are expensive and time-consuming to develop. Some longitudinal studies require data collection on the same animals over their lifetimes. Preventing nosocomial infection is paramount in maintaining the integrity of the research design and in preserving valuable laboratory stock for continued study.

Most research institutions invest substantial resources to keep these valuable animal assets safe. Microbial safety and cost factors are major issues associated with use of bedding materials for laboratory animals. Traditional corncob after it enters the lab animal facility leaves open the possibility that pathogenic bacteria are introduced to the facility in storage and handling before sterilization efforts. Using irradiated or pre-sanitized corncob essentially eliminates that risk because the corncob arrives at the facility with near sterile characteristics. However, the cost of irradiated corncob bedding can triple that of non-sanitized bedding, and autoclaving is widely understood to be costly, especially when energy costs are taken into account. The high costs of irradiating or autoclaving present an opportunity for applied science to achieve the same degree or better of near-sterility at a significantly lower cost.

The destruction of pathogenic bacteria, fungi and viruses in corncob particles can be achieved by rigorous chemical or physical methods required to destroy bacterial endospores. This is true because bacterial endospores exhibit the highest resistance to chemicals, heat or irradiation compared to other microorganisms including viruses.

Another, less common, method for sterilizing food is the tyndallization process, named after the 19th century scientist John Tyndall. Tyndallization essentially consists of heating the substance for 15 minutes for three days in a row (usually by boiling it). During the waiting periods over the three days, the substance being sterilized is kept at a warm room temperature; i.e., a temperature that is conducive to germination of the spores. On the second day most of the spores that survived the first day will have germinated into bacterial cells. These cells will be killed by the second day's heating. The third day kills bacterial cells from late-germinating spores. This process requires considerable time, and the material being treated must be maintained at the proper conditions over the entire 3-day period. Further, the tyndallization process is not considered reliably effective.

It is challenging to destroy bacterial endospores with interventions other than those previously mentioned which are costly, cumbersome, difficult to scale up, and raise questions about reliability. One approach to kill the endospores with greater practicability is to render them more susceptible to the inactivation method. One way to decrease spore resistance is to induce spore germination.

Accordingly, the overall goal of the present invention is to provide a novel process to substantially reduce or eliminate populations of bacterial endospores in corncob particles by exploiting their vulnerable state—after germination. Once germinated, spores have decreased resistance to chemicals, heat or irradiation.

Therefore, it is a primary object, feature, or advantage of the present invention to improve upon the state of the art.

It is a further objective, feature or advantage of the present invention to provide methods for substantially reducing or eliminating populations of bacterial endospores in fibrous material.

It is a further objective, feature or advantage of the present invention to provide methods for substantially reducing or eliminating populations of bacterial endospores in plant-fiber-rich (PFR) material by exploiting the vulnerable state of those spores when stimulated to germinate.

It is a further objective, feature or advantage of the present invention to provide reliable methods for reducing or eliminating populations of bacterial endospores in PFR material, wherein the process can be completed in less than one day, and preferably less than five hours.

It is a further objective, feature or advantage of the present invention to provide reliable methods for reducing or eliminating populations of bacterial endospores in PFR material, wherein the product of the process is a dry PFR material.

It is a further objective, feature or advantage of the present invention to provide PFR material, for example corncob particles, that has been sanitized by a process that substantially reduces or eliminates populations of bacterial endospores in corncob particles by exploiting the vulnerable state of those spores when stimulated to germinate.

It is a further objective, feature or advantage of the present invention to provide reliable methods for reducing or eliminating viruses in PFR material, wherein the product of the process is a dry fiber-rich material.

SUMMARY OF THE INVENTION

The present invention provides methods for sterilizing or substantially reducing or eliminating populations of bacterial endospores—the most resistant microbial life forms—in a material. In one aspect, the invention involves a method of sterilizing, substantially reducing, or eliminating populations of microbes in PFR material, comprising exposing the PFR material to a heat-shock of 65° to 90° C. for 10 to 30 minutes; and drying the PFR material by heating it. In one aspect, the PFR material is a bedding material, preferably corncob particles. In a preferred embodiment, the heat shock is about 80° C. for about 15 minutes. In another aspect, the heating comprises exposing the heat-shocked PFR material to a temperature of between about 115° and 155° C. for between about 25 and about 40 minutes.

In one embodiment, the method also involves adding a germinate to the PFR material prior to heat-shocking, wherein said germinant is effective to promote germination of bacterial endospores. In a preferred embodiment, the germinant is corn powder.

In another embodiment, the method also involves wetting the PFR material with water prior to heat shocking. In a preferred embodiment, the particles are coated with water that contains the germinate. In another embodiment, the method further involves holding the PFR material following the heat shocking, wherein said holding comprises incubating the PFR material at between about 35° and about 55° C. for 10 to 30 minutes. More preferably, the holding step involves maintaining the PFR material at an internal temperature of about 40° C. for at least 20 minutes. In a more preferred embodiment, the entire process may be performed in less than one day, and most preferably in less than five hours.

In another aspect, the present invention provides PFR material that is substantially free of microbes produced by the described methods. In a preferred embodiment, the PFR material is a bedding material, more preferably corncob particles. In a more preferred embodiment, the PFR material produced by the described methods has a viable microbe content of 10 or less $\log_{10}$ CFU/g of PFR material. In an even more preferred embodiment, the PFR material produced by the described methods has a viable microbe content of 1 or less $\log_{10}$ CFU/g of PFR material. In another aspect, the PFR material produced by the described methods is dry.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
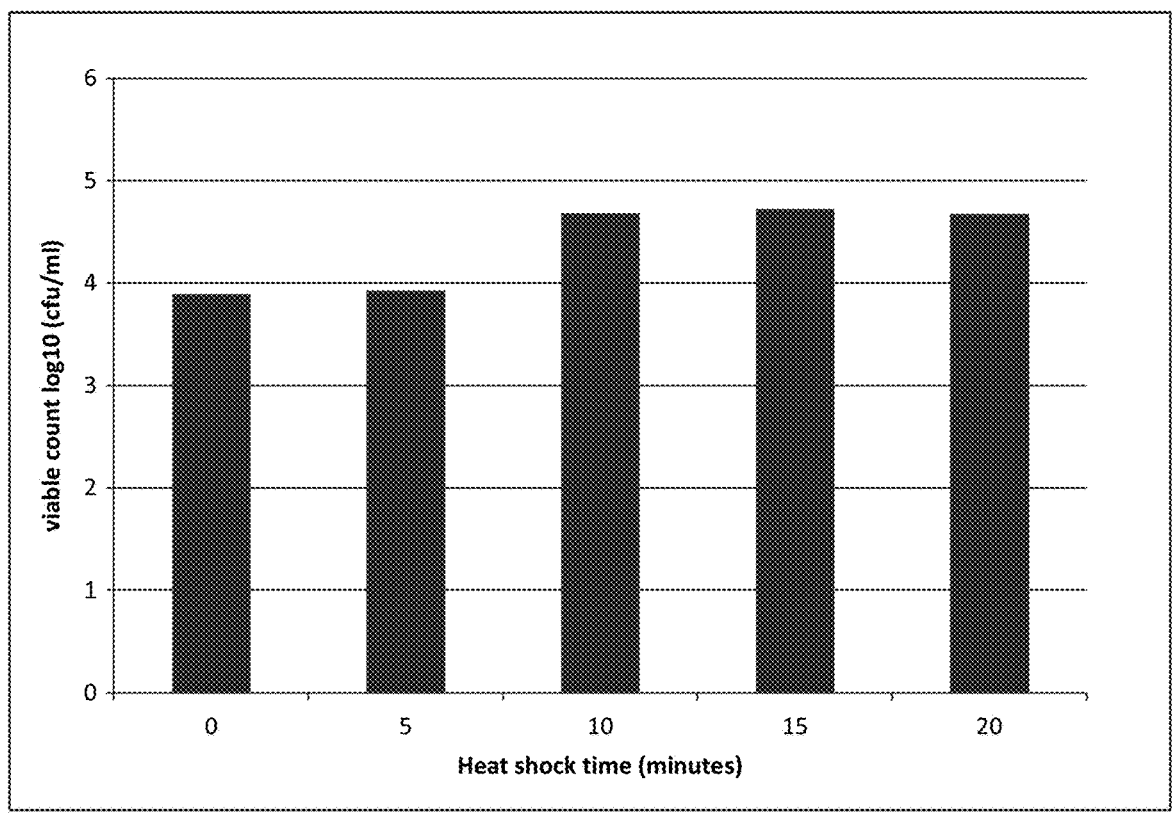
FIG. 1 (A-B) shows bacterial colony counts from spores that were heat shocked at 80° C. for various times in (A) water or in (B) wet corncob particles.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

Definitions

Units, prefixes, and symbols may be denoted in their SI accepted form. Numeric ranges recited within the specification are inclusive of the numbers defining the range and include each integer within the defined range. The terms defined below are more fully defined by reference to the specification as a whole.

As used herein, an "animal" is defined to include any organism kept as a pet or commonly housed in an animal care or animal housing or vivarium facilities, and especially animals that are kept in cages, including laboratory and research animals. Such animals include rodents, such as mice, rats, hamsters, gerbils, Guinea pigs, ferrets, and rabbits; birds such as a quails, chickens, turkeys, parrots, parakeets, canarys, and finchs; canines, such as domesticated dogs; felines, such as domesticated cats; and primates such as a monkeys, chimpanzees, rhesus macaques and gorillas.

"PFR material" refers to any substance that is primarily comprised of cellulose, hemicelluloses, pectins and/or other water-soluble and -insoluble plant fiber material. PFR material may be any material that is a component or derivative of an agricultural plant, including, for example, pressed wood pellets, wood shavings, kenaf, sawdust, wheat straw, barley straw, oat straw, timothy straw and various forage straws, and corncob particles. Included in, but not limited to, are the fiber-containing materials such as plant tubers, wheat, seed, shells of seeds, stems, roots, and leaves of plants, fruits and their skins, wood, tree branches, tree bark, straw, grass, and waste materials originating from the agricultural industry, for example, distiller's dry grain, sugar beet pulp, cellulose pulp, paper waste, cotton, linen, vegetables and vegetable waste, such as tomato skins and seeds, and the like. PFR material may also include cardboard products, such as for example recycled cardboard. "Bedding material" as used herein includes any type of PFR material that is commonly used within the field of animal husbandry. In a preferred embodiment, the bedding material is composed of corncob particles.

"Corncob particles" refers to a variety of corncob particle components of different types and sizes that have been prepared and fractionated from corncobs. Corncob particles may be derived from the cob's dense woody interior ring portion, e.g., in the form of broken granules known as corncob grit or grit granules or grit particles (or simply "grit"). Corncob particles may also be derived from pith, chaff and beewing portions of the cob. Corncob particles can have various grades, defined by the approximate percent of particles retained on test screens (U.S. Standard), with examples shown in Table 1. Reference to the size of corncob particles is based on these designations.

example, introducing 5 pounds of pulverized corn kernels to 2000 pounds of water. Germinants may also include culture media, such as, for example, lysogeny broth (LB; a.k.a. Luria broth, Lennox broth, or Luria-Bertani) medium, potato dextrose agar, Sabouraud agar, chocolate agar, nutrient agar, plate count agar, and the like.

"Substantial" or "substantially" with reference to decreasing, reducing or eliminating a material, including, for example, water or microbes refers to compositions completely lacking microbes or having such a small amount of the component that the component does not affect the performance of the composition. By way of example only, substantially eliminating microbes from a material could involve a reduction of microbes to or below the limit of detection of standard measurements.

Methods for Sterilizing, or Substantially Reducing or Eliminating Populations of Bacterial Endospores in PFR Material According to one aspect of the invention, methods are provided that decrease or eliminate microbes from PFR material, including bedding material. In a preferred embodiment, the processes substantially eliminate microbes from the PFR material.

In one embodiment, the method comprises exposing the PFR material to a first heat shocking step followed by a second heating step. The heat shocking step involves exposing the PFR material to a temperature between about 65° and

TABLE 1

Approximate percent of particles retained on test screens (U.S. Standard).

| Screen # | 1/4" | 1/8" | 1014 | 1020 | 1420 | 2040 | 4060 | -40 | 1440 PC | -40 PC |
|---|---|---|---|---|---|---|---|---|---|---|
| 6 | 45% | | | | | | | | | |
| 8 | 50% | | | | | | | | | |
| 10 | 5% | 30% | | | | | | | | |
| 14 | | 70% | 55% | 35% | | | | | | |
| 20 | | | 45% | 60% | 75% | | | | 30% | |
| 30 | | | 5% | 20% | 35% | | | | 40% | |
| 40 | | | | 5% | 60% | | | 10% | 30% | 10% |
| 50 | | | | | 5% | | | | | |
| 60 | | | | | | 90% | | | | |
| 80 | | | | | | 10% | | | | |
| Pan | | | | | | | | 90% | | 90% |

It is understood that the methods of sterilizing, or reducing or eliminating microbes are effective for all particle sizes. Corncobs are rich in plant fiber and are particularly suitable for bedding material. While other PFR materials might be used, corncobs are particularly well suited for the present application because of their absorbency, which is primarily due to the physico-chemical characteristics of the particles.

"Microbes" as used herein includes, but is not limited to bacteria, fungi, archaea, viruses and protozoans, such as, for example, yeast, molds and bacteria, including sporulating bacteria. Microbes include microorganisms naturally present in harvest, processing, storage, and transport of PFR material, including corncobs and corncob particles.

"Germinant" refers to a nutrient composition material that promotes microbial growth. Germinants include those derived from agricultural-based material such as, for example, baggasse powder, rice-straw powder, wheat bran, corncob powder, and corn powder. Germinants may also include organic nutrients in natural complexes or in isolation, such as, for example, malt extract, yeast extract, potato extract, inosine, glucose, glycine, L-alanine, L-serine, L-leucine, L-isoleucine, peptone, soya-peptone, bactopeptone, and corn steep water. Corn steep water refers to water to which powdered or pulverized corn has been introduced, for about 90° C. for 10 to 30 minutes. In a preferred embodiment, the heat shocking comprises exposure at about 80° C. for about 15 minutes.

According to one embodiment of the invention, the second heating step involves exposing the PFR material at greater than 115° C. In a preferred embodiment, the heating is at greater than 121° C. In a more preferred embodiment, the heating is between about 150° and 180° C. The heating step is carried out for a sufficient amount of time to adequately dry the material, depending on the temperature used. For example, the heating may be at 115° C. for 40 minutes, or at 155° C. for 25 minutes.

In one aspect, the heat shocking step and/or heating step may be performed using any technique that achieves the necessary temperature. For example, the heating may be performed using a fluidized sand bath, a water bath, a heating element, a conduction heater, an oven, or radiation heating such as infrared, ultraviolet, microwave, radio frequency, and high-frequency (HF) waves. In a preferred embodiment, the heat shocking step is performed using a water bath. In another preferred embodiment, the second heating step is performed using a forced-air convection oven/dryer.

In one embodiment, the PFR material may be treated prior to being subjected to the heat shocking and heating steps.

For example, the PFR material may be wetted or soaked, preferably with water. In a preferred embodiment, the PFR material may also be mixed with a germinant, for example by coating the PFR material with water containing a germinant. In a more preferred embodiment, the germinant is peptone solution, L-alanine solution, or corn steep water.

In one aspect, the methods may also include a holding step between the heat shocking and second heating steps, wherein the soaked PFR material is incubated at between about 35° and about 55° C. for 10 to 30 minutes. In a preferred embodiment, the PFR material maintains an internal temperature of about 40° C. for at least 20 minutes.

Sterilized PFR Material

In another aspect, the invention encompasses PFR material that results from the described processes, wherein the resulting PFR material is sanitized or sterile, and at least substantially free of microbes. In a preferred embodiment, the PFR material is corncob particles. In another preferred embodiment, the viable microbe content of the PFR material following processing is 10 or less CFU/g of PFR material.

In one aspect, the PFR material is dry flowing treatment by the described process. In a preferred embodiment, the PFR material has less than 20% moisture content following the described process. In a more preferred embodiment, the PFR material has less than 10% moisture content following the described process.

The following examples are intended for illustration purposes only and are not intended to limit the invention in any way.

EXAMPLES

Example 1: Extent of Germination of Bacterial Spores Following Heat-Shock Treatments in Sterile Water and in Sterile Wet Corncob Particles Bacterial spores are extremely heat resistant. Reliable heat inactivation of bacterial spores can be achieved by autoclaving which typically refers to the application of pressurized steam at 121° C., 15 psi, for about 20 minutes depending on the quantity of material to be treated. However, autoclaving can be costly, time consuming, and limited by the volumetric constraints of the autoclave. It is documented that bacterial spores (if triggered to germinate) exhibit decreased resistance to heat. Some bacterial spores will not germinate unless activated by heat-shock, which breaks spore dormancy. Sub-lethal heating (heat-shock) increases the number of bacterial spores that germinate within a spore population. Thus, it is important to determine the extent of germination of bacterial spores following heat-shock treatments in sterile water and in sterile wet corncob particles.

Sterilized water and corncob particles (⅛"; see Table 1) were inoculated with bacterial spores to give ~1×$10^5$ (5.0 log) spores per ml (water) or per gram (corncob particles). Bacterial spores were harvested from spore-forming bacteria isolated from traditional corncob particles and used to inoculate water to obtain ~$10^5$ colony forming units (CFU) per ml. The water was sterilized by autoclaving and cooled to ambient temperature (23° C.) before inoculation. Large tubes of water containing bacterial spores were heat-shocked at 65, 70, 80 and 90° C. in a thermostatically controlled water bath. The tubes of spore suspension were held at each heat-shock temperature for 10, 20, and 30 minutes before immersing them in an ice/water mixture. The exposure time represents the length of time that the samples have been exposed to the appropriate temperature. The come-up time (time required for samples to reach the appropriate temperature) within the test tube was recorded. Tubes of non-heat-shocked spore suspensions served as control.

Treatment conditions for water (heat-shock temperature and time) were also used in heat-shock experiments involving corncob particles. Samples (10-gram) of sterile corncob particles were placed in large test tubes. The particles were inoculated with bacterial spores to obtain ~$10^5$ CFU/g. In each tube the inoculated particles were soaked with 10 ml of sterile water and heat-shocked as previously described for bacterial spores in water.

Enumeration of bacterial colonies was performed to estimate the number of spores that germinated under each heat-shock condition (temperature and time). Microbial analyses were performed according to standard methods of analysis adapted from the Compendium of Methods for the Microbiological Examination of Foods, 4th edition (APHA, 2001). Numbers of spore-forming bacteria from heat-shocked and control spores in water or corncob particles were counted. Ten-fold serial dilutions of spores in water or corncob particles were prepared in buffered peptone water and aliquots of diluted suspension were surface-plated on dextrose tryptone agar (DTA). Inoculated DTA plates were incubated at 35° C. for 48 hours (for mesophilic aerobic spore-formers) and 55° C. for 48 to 72 hours (for thermophilic aerobic spore-formers).

Figure 1B:
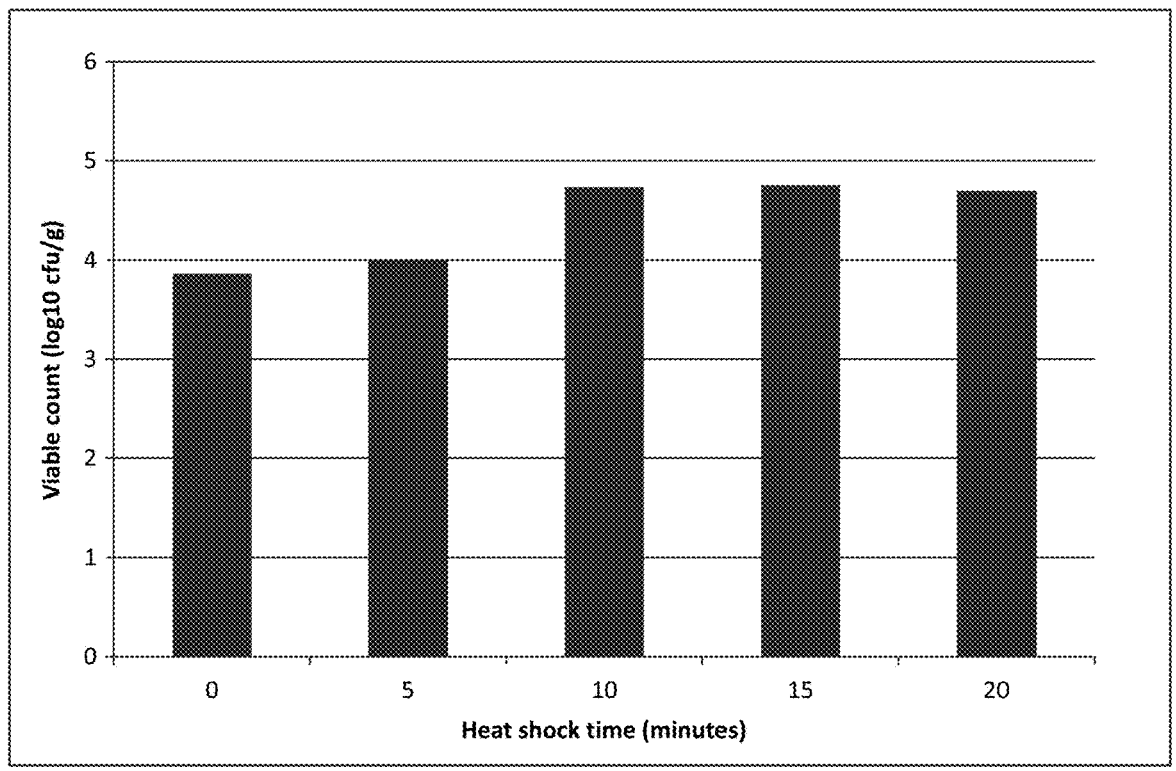

The extent of germination of bacterial spores following heat-shock of spores in water and wet corncob particles is shown in FIGS. 1A and 1B. Heat-shock at 80° C. for 10 or 15 minutes resulted in highest bacterial colony counts from the spores in water or corncob particles. There were no significant differences in colony counts at heat-shock treatments at 80° C. for 10, 15, and 20 minutes.

Heat-shock of spores in water or wet corncob particles at 80° C. for 10 to 20 minutes increases the extent of spore germination. This is based on the observed increase in bacterial colony counts from heat-shocked spores compared to control (23° C.; non-heat-shocked). The fact that heat-shock at 80° C. for 10 to 20 minutes produced bacterial colony counts ranging from 4.67 to 4.75 log CFU/ml or g (less than the 5.0 log initial spore count/ml or g) indicates that not all the spores germinated.

The length of time between heat-shock and germination of bacterial spores can vary among types of spores. Also, the optimal temperature for the germination process following heat-shock can vary among spores. Therefore, it is important to determine the influence of various post heat-shock holding times and temperature on the extent of germination of bacterial spores in corncob particles to further increase the extent of spore germination.

Example 2: Enterobacteriaceae, Yeast, Molds and Spore-Forming Bacteria Viability in Heat-Shocked and Non-Heat-Shocked Corncob Particles Corncob particles, like many raw agricultural products, are contaminated with organisms (other than spore-forming bacteria) such as Enterobacteriaceae, yeast and molds. One or more temperature/time combinations used for heat-shock may kill these microorganisms to reduce the microbial load of corncob particles.

To determine whether vegetative bacterial cells, yeast, and molds are capable of surviving the heating conditions used for heat-shock of bacterial spores in corncob particles, heat-shock temperature and time that produce the largest amount of spores that germinate (based on plate counts of spore-formers) were used in experiments to determine the effect of this procedure on the natural microbial content of traditional corncob particles. Enumeration of microbial groups (bacteria and fungi) was performed before and after heat-shock treatment. Briefly, the particles from each tube were aseptically transferred to separate sterile 250-ml screw-cap Erlenmeyer flasks. To each flask, 80 ml of sterile 0.1% (w/v) peptone were added. The flasks were vigorously shaken to remove microbial cells from the particles. Aliquots (0.1-ml or 1.0-ml) of wash solution were plated on appropriate agar media to determine numbers of viable microorganisms. Samples (10-gram) of sterile corncob particles were placed in large test tubes. In each tube the particles were soaked with 10 ml of sterile water and heat-shocked as previously described for bacterial spores in water.

Microbial analysis of corncob particles (heat-shocked and non-heat-shocked) was performed as previously described. Appropriate nutrient agar plates, plating technique and incubation conditions used to obtain viable counts of specific microbial groups are provided in Table 2.

TABLE 2

Agar media, plating technique, and incubation conditions for microbiological tests to be performed on heat-shocked and non-heat-shocked corncob particles

| Microbial Test | Agar Media | Plating Technique | Incubation Conditions |
| --- | --- | --- | --- |
| Aerobic plate count | PCA | Surface plate | 30° C. (86° F.), 48 hours |
| Enterobacteriaceae | TSA/VRB overlay | Pour plate | 35° C. (95° F.), 24 hours |
| Mesophilic aerobic spore-formers | DTA | Surface plate | 35° C. (95° F.), 24 hours |
| Thermophilic aerobic spore-formers | DTA | Surface plate | 55° C. (131° F.), 48-72 hours |
| Yeast and molds | DRBC agar | Surface plate | 25° C. (77° F.), 5 days |

Figure 2:
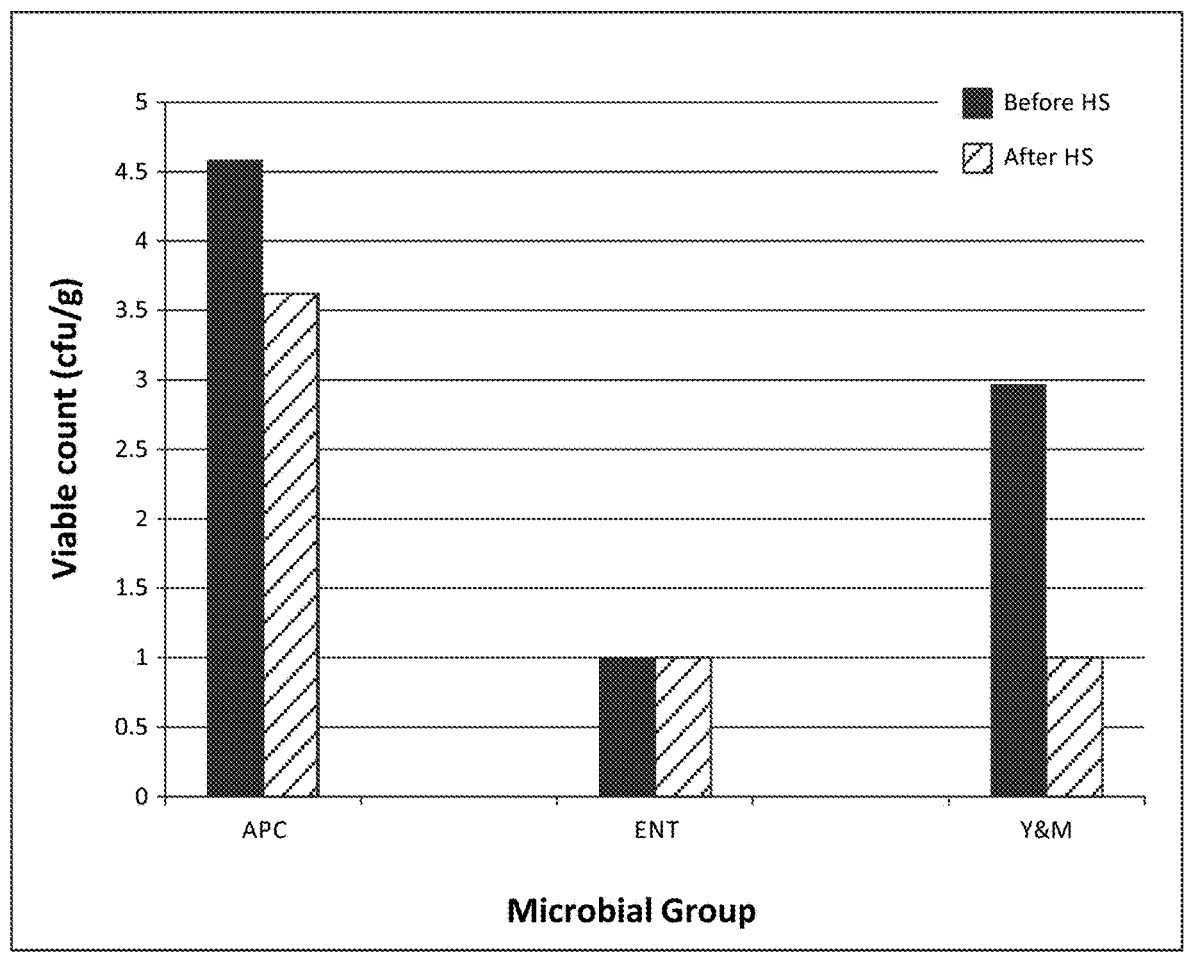
FIG. 2 shows aerobic plate count (total count; APC), Enterobacteriaceae (ENT) and yeast and mold (Y&M) counts in wet ⅛" corncob particles (see Table 1) before and after heat shock (HS) at 80° C. for 15 minutes.

PCA = plate count agar;
DTA = dextrose tryptone agar;
TSA = tryptic soy agar;
VRB = violet red bile agar;
DRBC = dichloran rose bengal chloramphenicol agar Aerobic plate count (total count) and counts of Enterobacteriaceae (ENT) and fungi (yeast and molds—YM) following heat-shock (80° C. for 15 minutes) in wet corncob particles are shown in FIG. 2. Heat-shock treatment of the wet particles decreased the aerobic plate count by approximately 0.97 log CFU/g. Numbers of viable ENT were below the detection limit (<10 CFU/g) in both heat-shocked and control samples. Viable YM were destroyed by the heat-shock treatment; none were detected in heat-shocked particles.

The aerobic plate count of the corncob particles gives an estimate of all viable vegetative cells that are able to grow aerobically under the conditions (agar medium, and incubation temperature and time) used in the present study. Bacterial spores that germinate (without heat-shock) and produce vegetative cells that form colonies on the agar medium also contribute to the aerobic plate count of non-heat-shocked particles.

Vegetative cells of bacteria and fungi are easily killed by temperatures that are merely used to heat-shock bacterial spores. Therefore, the decrease in aerobic plate count (0.97 log CFU/g) in the corncob particles after heat-shock at 80° C. for 15 minutes is likely due to death of the more susceptible vegetative cells. All the bacterial colonies on agar-plated heat-shocked samples were from spore-forming bacteria. This is not surprising because bacterial spores make up a substantial part of the microbial population of dried corncob particles.

The absence or very low numbers (<10 CFU/g) of Enterobacteriaceae in the control corncob particles indicate that intestinal pathogens such as *Salmonella enterica*, *Shigella*, and *Escherichia coli* are absent. Enterobacteriaceae was isolated from some of the whole corncobs, but not from the ground corncob particles (⅛") in the batch provided for the present study.

Contamination of whole corncobs with Enterobacteriaceae from feces of birds, rodents or insects that frequent the corncob piles might be sporadic, and contaminating microbes are likely diluted out during the processing of the corncobs to produce the particles. Also, some of those organisms probably died from the very harsh dry conditions of processing.

Like bacterial vegetative cells, many yeast and molds are easily destroyed by temperatures used to heat-shock bacterial spores. Results of the present study suggest that contaminating fungi in corncob particles could be eliminated during the heat-shock part of the manufacturing process for sanitized corncob particles.

Example 3: Effect of Holding Temperature and Time (Post Heat-Shock) on the Extent of Germination of Bacterial Spores in Corncob Particles After bacterial spores are heat-shocked, the length of time for the start of germination can vary among spores in a population. Also, the ideal post-heat-shock temperature for germination may vary depending on whether the spores are mesophilic or thermophilic. Since both groups of spores are present in corncob particles, it was important to determine temperature/time conditions that produced the maximum amount of germinating spores of both groups to enhance their destruction.

The extent of germination of heat-shocked bacterial spores is dependent on post heat-shock conditions of temperature and length of time at a specified temperature. Sterile water and corncob particles were inoculated with bacterial spores and heat-shocked as described above. Following heat-shock, the samples were placed in a 50/50 ice/water mixture. Temperature of the samples of water and corncob particles was monitored using thermocouples placed in separate tubes of non-inoculated samples. When internal temperature of the samples reached 35°, 40°, 45°, or 55° C., the tubes were transferred to water baths (set at appropriate temperatures) and held at a specific temperature for 0 (control), 10, 20 or 30 minutes before performing microbial analysis.

Ten-fold serial dilutions of spores in water or corncob particles were prepared in buffered peptone water and aliquots of diluted suspension were surface-plated on dextrose tryptone agar (DTA). Inoculated DTA plates were incubated at 35° C. for 48 hours (for mesophilic aerobic spore-formers) and 55° C. for 48 to 72 hours (for thermophilic aerobic spore-formers).

Figure 3:
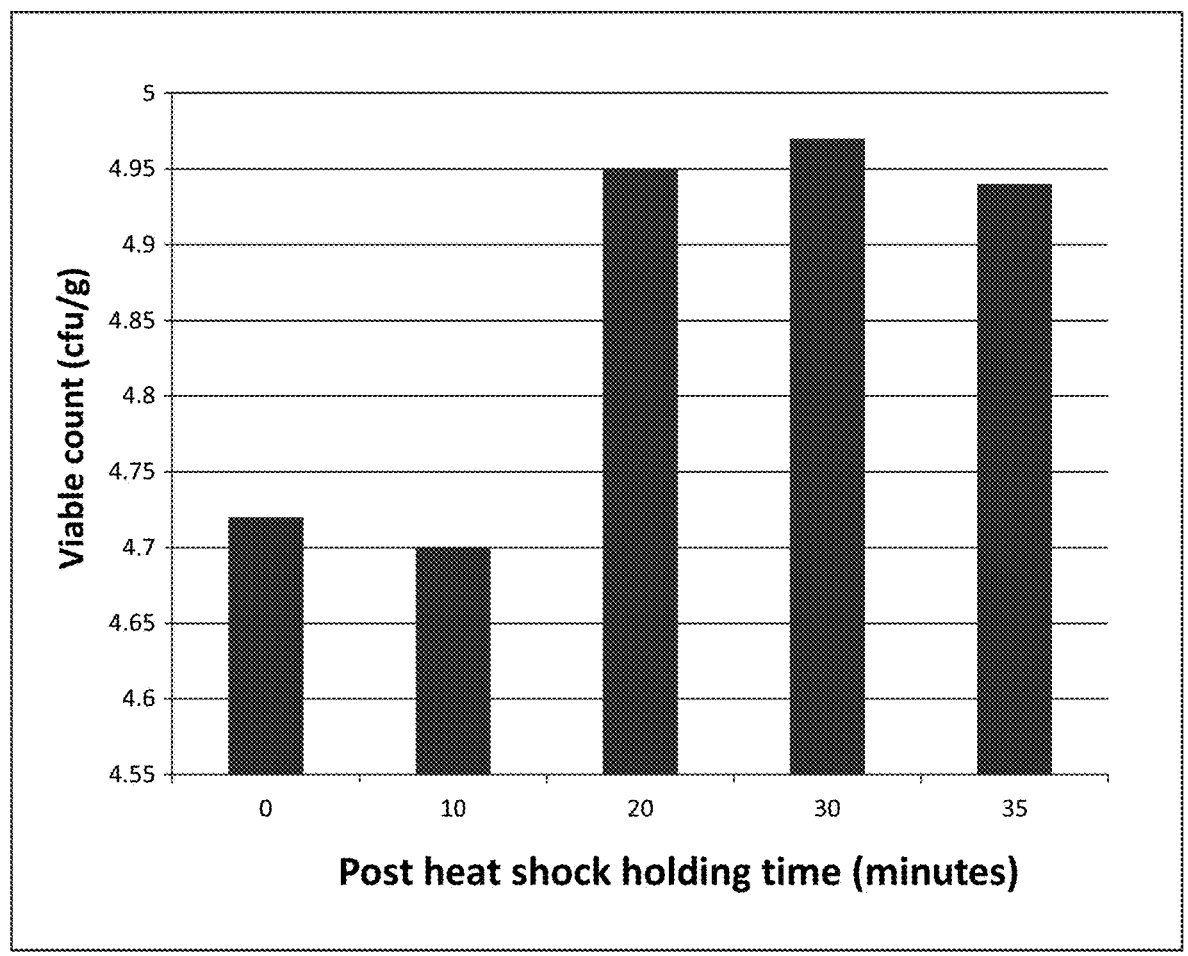
FIG. 3 shows the effect of holding time at the best holding temperature (40° C.) on germination of bacterial spores in wet artificially inoculated ⅛" corncob particles.

Results are shown in FIG. 3. The post heat-shock conditions of 40° C. (for 20 minutes or longer) resulted in the highest amount of spore germination compared to other temperature and time conditions used in the present study. At a holding temperature of 40° C., there were no significant differences in the extent of spore germination at 20, 30 or 35 minutes.

When bacterial spores are heat-shocked to trigger germination, their enzymes become active and set the process of spore germination in action. Since enzyme activity is affected by temperature, certain temperatures may stop, slow down or increase the spore germination process. Therefore, to optimize germination, the best post-heat-shock holding temperature and time needed to be determined. Based on these results, cooling the heat shocked corncob particles to 40° C. and holding them at that temperature for a minimum time of 20 minutes were the best conditions for increasing the extent of germination of bacterial spores in wet 1/8" corncob particles.

Example 4: Viability of Bacterial Spores after High Temperature Drying of Heat-Shocked and Non-Heat Shocked Corncob Particles To determine whether heat-shocked bacterial spores in corncob particles are more readily destroyed by high temperature drying compared to non-heat-shocked spores, optimized conditions of heat-shock and post-heat-shock holding temperature and time obtained from experiments described in Examples 1, 2, and 3, were used to determine the viability of bacterial spores after high temperature drying of heat-shocked and non-heat-shocked (control) corncob particles.

Corncob particles (1/8") were sterilized by autoclaving. The sterilized particles were inoculated with bacterial spores to give ~1×10$^5$ (5.0 log) spores per gram. Spores in corncob particles were heat-shocked at 80° C. for 15 minutes as previously described. Following heat-shock the inoculated particles were cooled to 40° C. and held at that temperature for 20 minutes before drying them at 176.6° C. for about 20 minutes.

Fifty-gram portions of wet corncob particles that had been subjected to heat-shock or non-heat-shocked control were placed in separate dishes. Both sets of particles were dried by heating in a forced-air convection oven/dryer at 176.6° C. for approximately 15 to 20 minutes. The particles were held for 30 minutes at ambient temperature in a laminar flow hood before analyzing them for numbers of viable bacterial spores and microbial vegetative cells. Particles that were not dried in the oven served as control and were used to determine the initial spore count in the corncob particles. The control and oven-dried particles were held for 30 minutes at ambient temperature (23° C.±1° C.) in a laminar flow hood before analyzing them for numbers of viable bacterial spores based on bacterial colony counts on dextrose tryptone agar.

Twenty five-gram samples of corncob particles were aseptically placed into separate sterile stomacher bags and mixed with buffered peptone water (225 ml per sample). The mixtures were vigorously shaken by hand for 30 seconds and ten-fold serial dilutions of the wash solution were prepared in 0.1% peptone water. Aliquots (1.0- or 0.1-ml) from the wash solutions or from selected dilutions of the wash solutions were plated onto appropriate agar media to determine the numbers of microorganisms (including spore-formers) in the particles.

Figure 4:
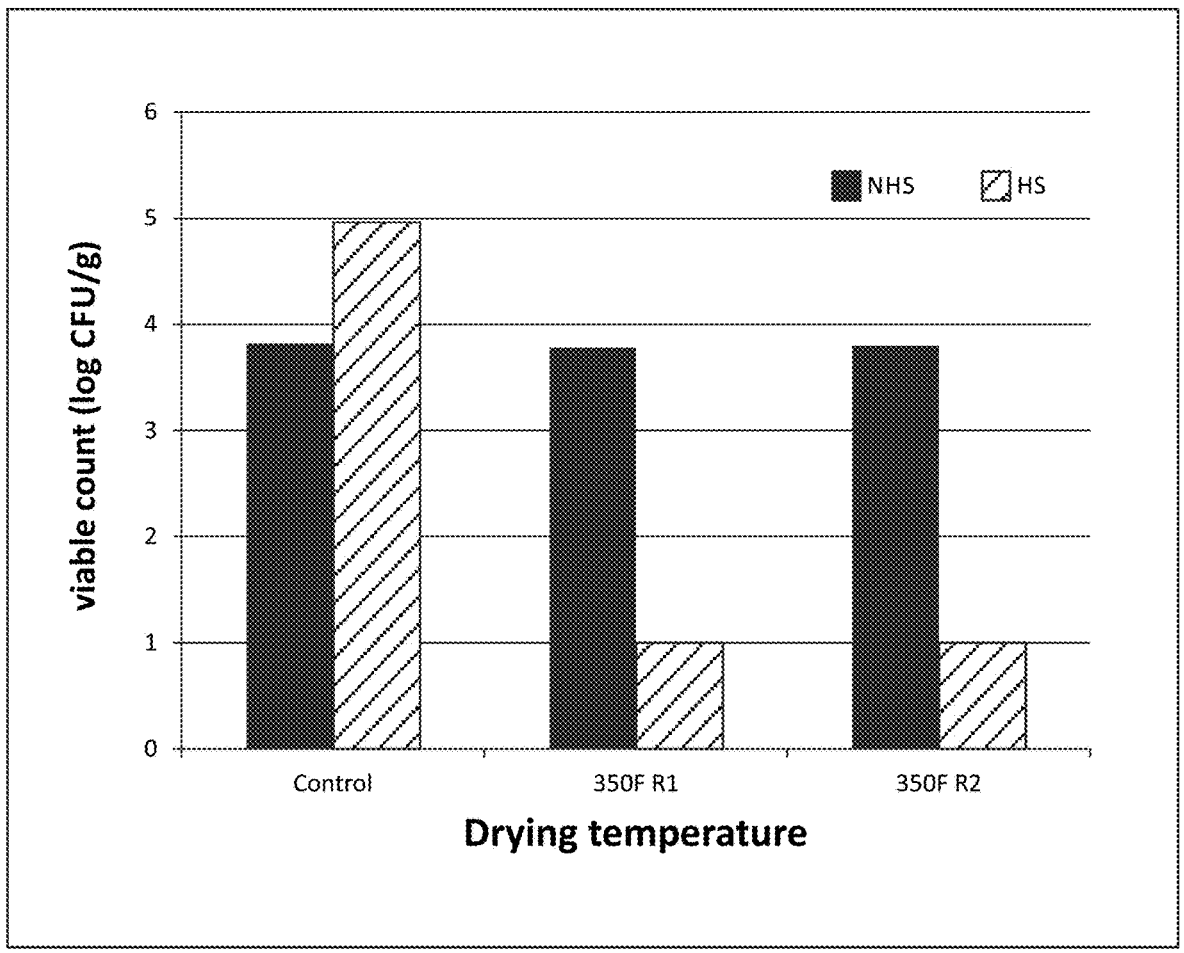
FIG. 4 shows viability of bacterial spores after drying of heat-shocked (HS) and non-heat shocked (NHS) wet corncob particles at 176.6° C. for 20 minutes.

In corncob particles that were not oven-dried, numbers of bacterial colonies from heat-shocked spores were higher than those from non-heat-shocked spores. Numbers of bacterial colonies from non-heat-shocked spores in corncob particles remained relatively constant during the drying process. Viable counts were 3.82, 3.78, and 3.80 log CFU/g, in control particles (not oven-dried), oven-dried particles (Rep 1) and oven-dried particles (Rep 2), respectively (FIG. 4).

The viability of heat-shocked (80° C., 15 minutes) bacterial spores which were held at 40° C. for 20 minutes, was destroyed during oven-drying at 176.6° C. for ~20 minutes. Over two trials of the experiment viable bacterial counts were beyond the detection limit (<10 CFU/g).

Based on the higher numbers of bacterial colonies that resulted from heat-shocked spores compared to those of non-heat-shocked spores, the heat-shocking of bacterial spores in corncob particles under conditions used herein increased the extent of spore germination.

Complete destruction of non-germinating bacterial spores cannot be achieved by the drying temperature and time (176.6° C. for ~20 minutes) described here. This is supported by data presented herein showing that the spore-forming bacterial count in corncob particles (with non-heat-shocked spores) was not changed during drying (FIG. 4). In contrast, viable bacterial counts were below the level of detection in particles that contained heat-shocked spores and subjected to those same drying conditions. These results indicate that these heat-shock conditions and post-heat-shock holding conditions can sensitize bacterial spores to heat and thus inactivate the spores during drying of corncob particles at 176.6° C. for ~20 minutes.

Example 5: Optimizing Germination and Heat Destruction of Bacterial Spores to Sanitize PFR Material The results of the above examples demonstrate the efficacy of the described sanitization method. However, the Inventors sought to optimize the process. Accordingly, the present example describes the optimization of heat-shock parameters on the natural microbial content of traditional corncob particles, and the minimum oven drying temperature required to achieve destruction of heat-shocked bacterial spores in naturally contaminated corncob particles.

Traditional corn cob particles were subjected to heating at 80° C. for 15 minutes to heat-shock bacterial spores. Before heat treatment, the corncob particles were wetted with filter-sterilized water to obtain initial amounts of added water ranging from 30% to 65% (w/w). After heat-shock, the particles were tempered at 40° C. (104° F.) for ~20 to 25 minutes before drying them in a convection oven/dryer.

To evaluate the effect of oven drying temperature, fifty-gram portions of wet corncob particles (heat-shocked and non-heat-shocked control) were placed in separate sterile aluminum trays. Both sets of particles were dried by heating in a forced-air convection oven/dryer at 82, 93, 104, 115, 121 and 155° C. During heating at a specified temperature the particles were removed at set times (20, 25, 30, 35, and 40 minutes), tempered to ~22±1° C. for 30 minutes in a laminar flow biological hood (with the fan on), then analyzed for numbers of viable bacterial spores based on colony counts of spore-forming bacteria.

To evaluate the effect of heat-shock treatment on the numbers of viable bacteria in corncob particles, samples of particles were analyzed for the following microbial groups: aerobic mesophilic bacteria, Enterobacteriaceae, yeast and molds, aerobic mesophilic spore-formers and aerobic thermophilic spore-formers before and after heat-shock, as described above.

Figure 5A:
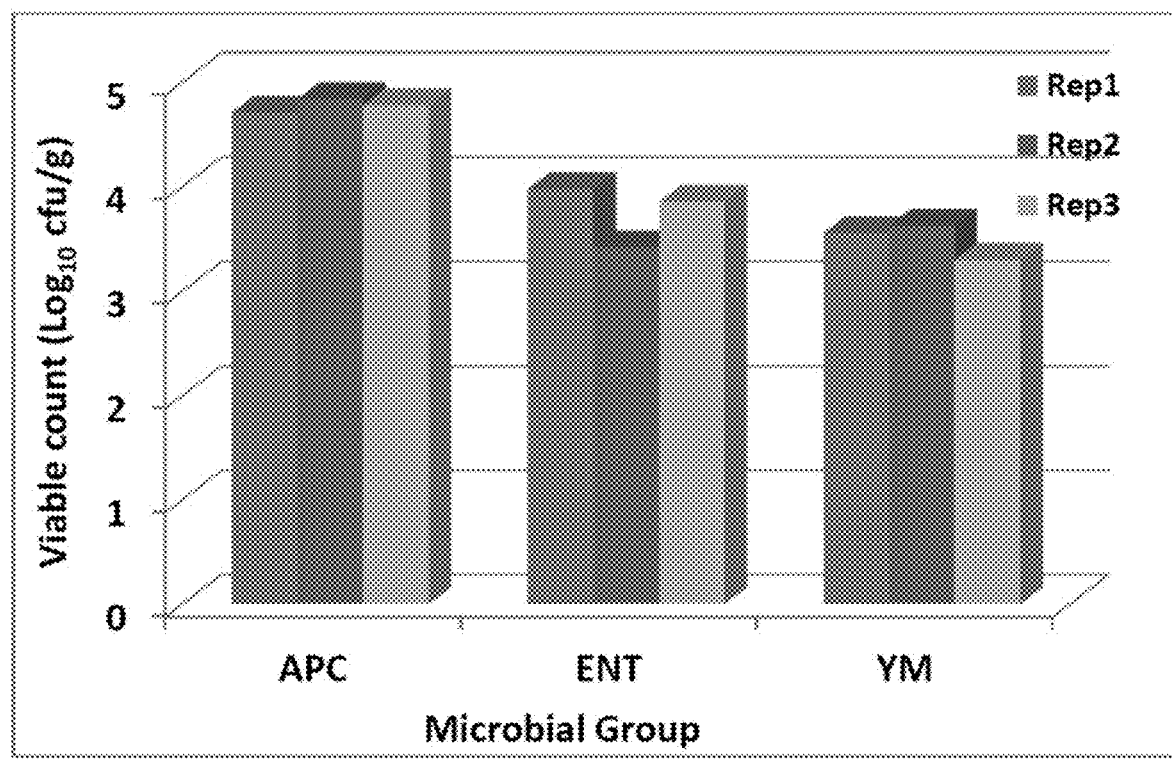
FIG. 5 (A-C) shows viable counts of aerobic mesophilic bacteria (APC), Enterobacteriaceae (ENT) and yeast and molds (YM) in naturally contaminated corncob particles. (A) Viable counts of aerobic mesophilic bacteria, Enterobacteriaceae and yeast and molds in naturally contaminated corncob particles before heat-shock. (B) Numbers of viable aerobic mesophilic bacteria, Enterobacteriaceae and yeast and molds in naturally contaminated corncob particles after application of heat-shock treatment of 80° C. for 15 minutes. (C) Numbers of viable aerobic mesophilic sporeformers (AMS) and aerobic thermophilic sporeformers (ATS) in naturally contaminated corncob particles after application of heat-shock treatment 80° C. for 15 minutes.

FIG. 5A shows numbers of viable aerobic mesophilic bacteria, Enterobacteriaceae, and yeast and molds in naturally contaminated corncob particles (1/8") before application of heat-shock treatment. Viable numbers of aerobic mesophilic bacteria, Enterobacteriaceae and yeast and mold, ranged from 4.71 to 4.84, 3.42 to 3.98, and 3.30 to 3.63 $\log_{10}$ CFU/g of corncob particles, respectively.

Figure 5B:
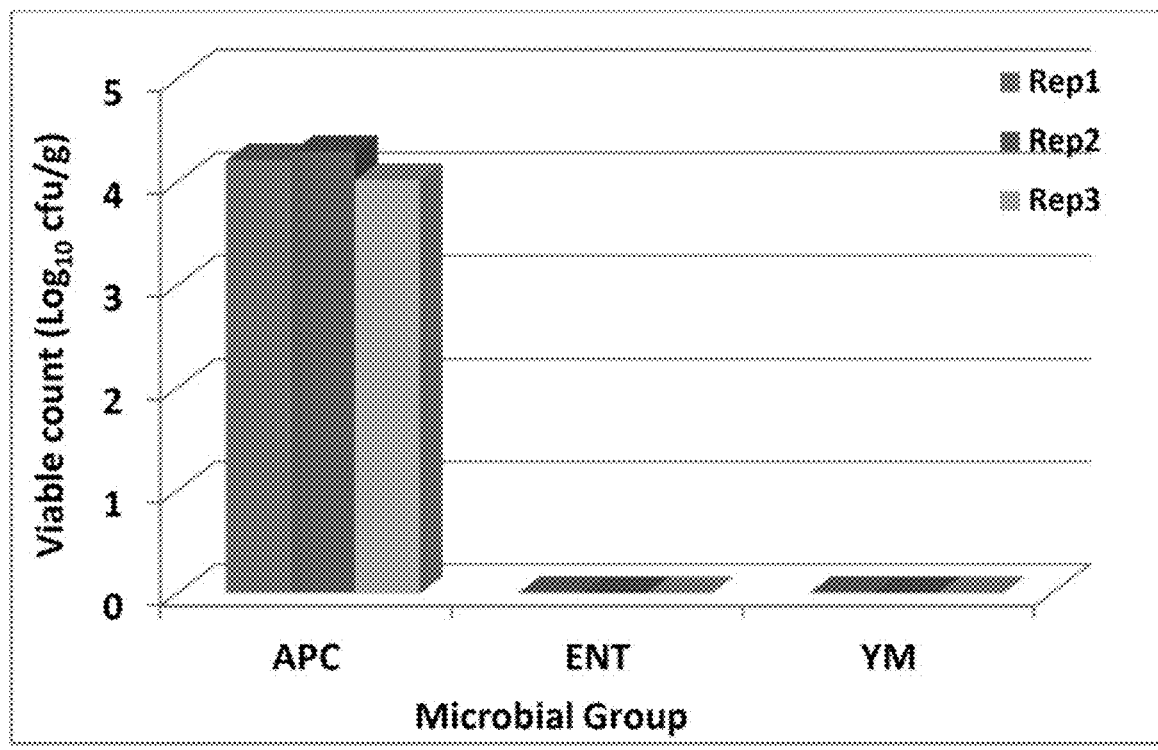

FIG. 5B shows numbers of viable aerobic mesophilic bacteria, Enterobacteriaceae, and yeast and molds in naturally contaminated corncob particles (⅛") after application of heat-shock treatment (80° C. for 15 minutes). Viable numbers of aerobic mesophilic bacteria ranged from 4.02 to 4.29 $\log_{10}$ CFU/g of corncob particles. No Enterobacteriaceae or yeast and molds were detected following heat shock.

Figure 5C:
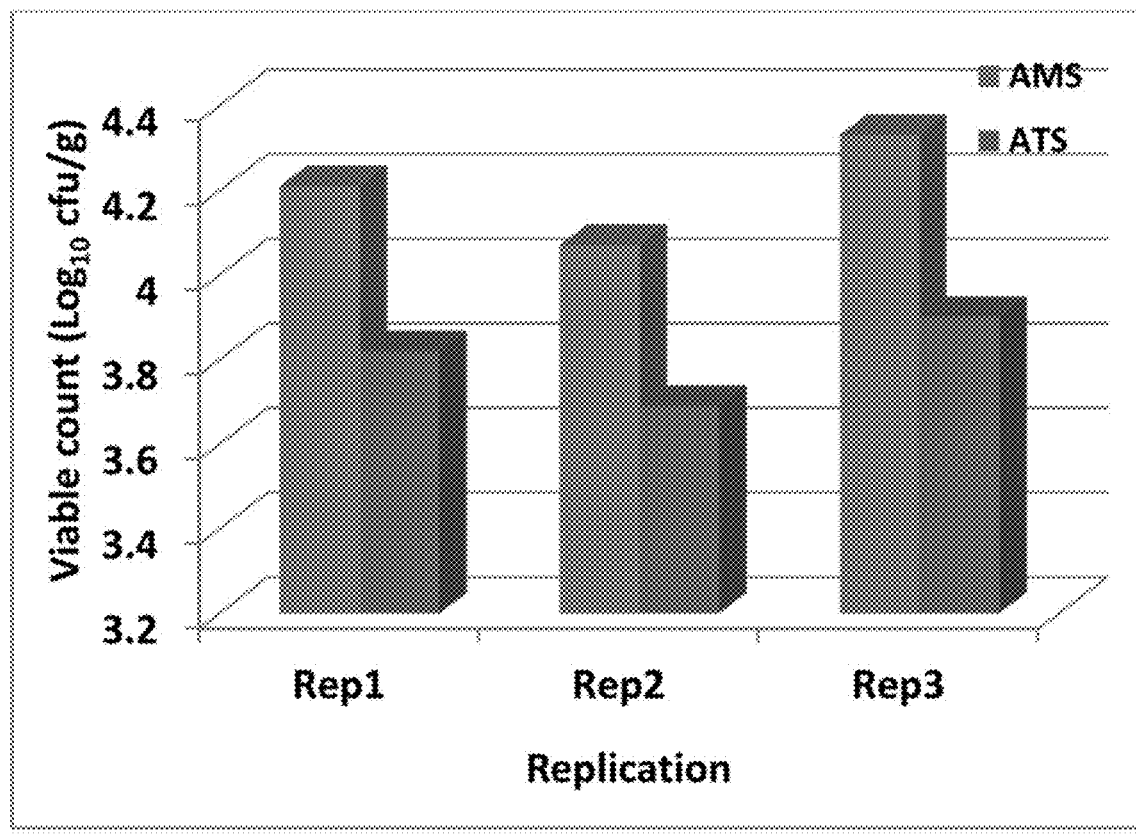

FIG. 5C shows numbers of viable aerobic mesophilic spore-formers and aerobic thermophilic spore-formers in naturally contaminated corncob particles (⅛") after application of heat-shock treatment (80° C. for 15 minutes). Levels of thermophilic spore-formers in naturally contaminated corncob particles (⅛") were consistently lower than those of mesophilic spore-formers. Numbers of viable aerobic mesophilic spore-formers and aerobic thermophilic spore-formers, in heat-shocked particles ranged from 4.07 to 4.33 and 3.69 to 3.90 $\log_{10}$ CFU/g, respectively.

Tables 3 to 10 show the effects of drying temperature and time on spore viability of aerobic mesophilic bacteria in non-heat-shocked (NHS) and heat-shocked (HS) naturally contaminated corncob particles (⅛) with 30 to 65% (w/w) added water. Non-heat-shocked spores (mesophilic) were totally unaffected by the heat applied for drying of the corncob particles. Similar results were obtained for thermophilic spores (data not shown)

The culture method used had a detection limit of 10 CFU/g of corncob particles.

TABLE 3

Influence of drying temperature and time on the spore viability of aerobic mesophilic bacteria in naturally contaminated corncob particles with 30% (w/w) added water.

| Temperature of Drying | Prior heat-shock | Drying time at specified temperature | | | | |
|---|---|---|---|---|---|---|
| | | 20 min | 25 min | 30 min | 35 min | 40 min |
| 82° C. | NHS | +++ | +++ | +++ | +++ | +++ |
| | HS | +++ | +++ | +++ | +++ | +++ |
| 93° C. | NHS | +++ | +++ | +++ | +++ | +++ |
| | HS | +++ | +++ | +++ | +++ | +++ |
| 104° C. | NHS | +++ | +++ | +++ | +++ | +++ |
| | HS | +++ | +++ | +++ | +++ | +++ |
| 115° C. | NHS | +++ | +++ | +++ | +++ | +++ |
| | HS | +++ | +++ | +++ | +++ | +++ |
| 121° C. | NHS | +++ | +++ | +++ | +++ | +++ |
| | HS | +++ | +++ | +++ | +++ | +++ |
| 176.6° C. | NHS | +++ | +++ | n/a | n/a | n/a |
| | HS | +++ | +++ | n/a | n/a | n/a |

Non-heat-shocked (NHS) and heat-shocked (HS)
Detection (+) or no detection (−) of viable spores based on bacterial colony counts
Each sign (+ or −) represents results of one replication of the experiment
n/a = not applicable; no data collected.

TABLE 4

Influence of drying temperature and time on the spore viability of aerobic mesophilic bacteria in naturally contaminated corncob particles with 35% (w/w) added water.

| Temperature of Drying | Prior heat-shock | Drying time at specified temperature | | | | |
|---|---|---|---|---|---|---|
| | | 20 min | 25 min | 30 min | 35 min | 40 min |
| 82° C. | NHS | +++ | +++ | +++ | +++ | +++ |
| | HS | +++ | +++ | +++ | +++ | +++ |
| 93° C. | NHS | +++ | +++ | +++ | +++ | +++ |
| | HS | +++ | +++ | +++ | +++ | +++ |

TABLE 4-continued

Influence of drying temperature and time on the spore viability of aerobic mesophilic bacteria in naturally contaminated corncob particles with 35% (w/w) added water.

| Temperature of Drying | Prior heat-shock | Drying time at specified temperature | | | | |
|---|---|---|---|---|---|---|
| | | 20 min | 25 min | 30 min | 35 min | 40 min |
| 104° C. | NHS | +++ | +++ | +++ | +++ | +++ |
| | HS | +++ | +++ | +++ | +++ | +++ |
| 115° C. | NHS | +++ | +++ | +++ | +++ | +++ |
| | HS | +++ | +++ | +++ | +++ | ++− |
| 121° C. | NHS | +++ | +++ | +++ | +++ | +++ |
| | HS | +++ | +++ | +++ | +++ | +−− |
| 176.6° C. | NHS | +++ | +++ | n/a | n/a | n/a |
| | HS | ++− | +−− | n/a | n/a | n/a |

Non-heat-shocked (NHS) and heat-shocked (HS)
Detection (+) or no detection (−) of viable spores based on bacterial colony counts
Each sign (+ or −) represents results of one replication of the experiment
n/a = not applicable; no data collected.

TABLE 5

Influence of drying temperature and time on the spore viability of aerobic mesophilic bacteria in naturally contaminated corncob particles with 40% (w/w) added water.

| Temperature of Drying | Prior heat-shock | Drying time at specified temperature | | | | |
|---|---|---|---|---|---|---|
| | | 20 min | 25 min | 30 min | 35 min | 40 min |
| 82° C. | NHS | +++ | +++ | +++ | +++ | +++ |
| | HS | +++ | +++ | +++ | +++ | +++ |
| 93° C. | NHS | +++ | +++ | +++ | +++ | +++ |
| | HS | +++ | +++ | +++ | +++ | +++ |
| 104° C. | NHS | +++ | +++ | +++ | +++ | +++ |
| | HS | +++ | +++ | +++ | +++ | ++− |
| 115° C. | NHS | +++ | +++ | +++ | +++ | +++ |
| | HS | +++ | +++ | +++ | +−− | −−− |
| 121° C. | NHS | +++ | +++ | +++ | +++ | +++ |
| | HS | +++ | +++ | +++ | −−− | −−− |
| 176.6° C. | NHS | −−− | −−− | n/a | n/a | n/a |
| | HS | ++− | +−− | n/a | n/a | n/a |

Non-heat-shocked (NHS) and heat-shocked (HS)
Detection (+) or no detection (−) of viable spores based on bacterial colony counts
Each sign (+ or −) represents results of one replication of the experiment
n/a = not applicable; no data collected.

TABLE 6

Influence of drying temperature and time on the spore viability of aerobic mesophilic bacteria in naturally contaminated corncob particles with 45% (w/w) added water.

| Temperature of Drying | Prior heat-shock | Drying time at specified temperature | | | | |
|---|---|---|---|---|---|---|
| | | 20 min | 25 min | 30 min | 35 min | 40 min |
| 82° C. | NHS | +++ | +++ | +++ | +++ | +++ |
| | HS | +++ | +++ | +++ | +++ | +++ |
| 93° C. | NHS | +++ | +++ | +++ | +++ | +++ |
| | HS | +++ | +++ | +++ | +++ | +++ |
| 104° C. | NHS | +++ | +++ | +++ | +++ | +++ |
| | HS | +++ | +++ | +++ | ++− | +−− |
| 115° C. | NHS | +++ | +++ | +++ | +++ | +++ |
| | HS | +++ | +++ | +++ | −−− | −−− |
| 121° C. | NHS | +++ | +++ | +++ | +++ | +++ |
| | HS | +++ | +++ | ++− | −−− | −−− |
| 176.6° C. | NHS | +++ | +++ | n/a | n/a | n/a |
| | HS | −−− | −−− | n/a | n/a | n/a |

Non-heat-shocked (NHS) and heat-shocked (HS)
Detection (+) or no detection (−) of viable spores based on bacterial colony counts
Each sign (+ or −) represents results of one replication of the experiment
n/a = not applicable; no data collected.

TABLE 7

Influence of drying temperature and time on the spore viability of aerobic mesophilic bacteria in naturally contaminated corncob particles with 50% (w/w) added water.

| Temperature of Drying | Prior heat-shock | Drying time at specified temperature | | | | |
|---|---|---|---|---|---|---|
| | | 20 min | 25 min | 30 min | 35 min | 40 min |
| 82° C. | NHS | +++ | +++ | +++ | +++ | +++ |
| | HS | +++ | +++ | +++ | +++ | +++ |
| 93° C. | NHS | +++ | +++ | +++ | +++ | +++ |
| | HS | +++ | +++ | +++ | +++ | +++ |
| 104° C. | NHS | +++ | +++ | +++ | +++ | +++ |
| | HS | +++ | +++ | +++ | ++- | --- |
| 115° C. | NHS | +++ | +++ | +++ | +++ | +++ |
| | HS | +++ | +++ | +++ | --- | --- |
| 121° C. | NHS | +++ | +++ | +++ | +++ | +++ |
| | HS | +++ | +++ | ++- | --- | --- |
| 176.6° C. | NHS | +++ | +++ | n/a | n/a | n/a |
| | HS | --- | --- | n/a | n/a | n/a |

Non-heat-shocked (NHS) and heat-shocked (HS)
Detection (+) or no detection (−) of viable spores based on bacterial colony counts
Each sign (+ or −) represents results of one replication of the experiment
n/a = not applicable; no data collected.

TABLE 8

Influence of drying temperature and time on the spore viability of aerobic mesophilic bacteria in naturally contaminated corncob particles with 55% (w/w) added water.

| Temperature of Drying | Prior heat-shock | Drying time at specified temperature | | | | |
|---|---|---|---|---|---|---|
| | | 20 min | 25 min | 30 min | 35 min | 40 min |
| 82° C. | NHS | +++ | +++ | +++ | +++ | +++ |
| | HS | +++ | +++ | +++ | +++ | +++ |
| 93° C. | NHS | +++ | +++ | +++ | +++ | +++ |
| | HS | +++ | +++ | +++ | +++ | +++ |
| 104° C. | NHS | +++ | +++ | +++ | +++ | +++ |
| | HS | +++ | +++ | +++ | ++- | --- |
| 115° C. | NHS | +++ | +++ | +++ | +++ | +++ |
| | HS | +++ | +++ | +++ | --- | --- |
| 121° C. | NHS | +++ | +++ | +++ | +++ | +++ |
| | HS | +++ | +++ | +-- | --- | --- |
| 176.6° C. | NHS | +++ | +++ | n/a | n/a | n/a |
| | HS | --- | --- | n/a | n/a | n/a |

Non-heat-shocked (NHS) and heat-shocked (HS)
Detection (+) or no detection (−) of viable spores based on bacterial colony counts
Each sign (+ or −) represents results of one replication of the experiment
n/a = not applicable; no data collected.

TABLE 9

Influence of drying temperature and time on the spore viability of aerobic mesophilic bacteria in naturally contaminated corncob particles with 60% (w/w) added water.

| Temperature of Drying | Prior heat-shock | Drying time at specified temperature | | | | |
|---|---|---|---|---|---|---|
| | | 20 min | 25 min | 30 min | 35 min | 40 min |
| 82° C. | NHS | +++ | +++ | +++ | +++ | +++ |
| | HS | +++ | +++ | +++ | +++ | +++ |
| 93° C. | NHS | +++ | +++ | +++ | +++ | +++ |
| | HS | +++ | +++ | +++ | +++ | +++ |
| 104° C. | NHS | +++ | +++ | +++ | +++ | +++ |
| | HS | +++ | +++ | +++ | ++- | --- |
| 115° C. | NHS | +++ | +++ | +++ | +++ | +++ |
| | HS | +++ | +++ | +++ | --- | --- |
| 121° C. | NHS | +++ | +++ | +++ | +++ | +++ |
| | HS | +++ | +++ | --- | --- | --- |
| 176.6° C. | NHS | +++ | +++ | n/a | n/a | n/a |
| | HS | --- | --- | n/a | n/a | n/a |

Non-heat-shocked (NHS) and heat-shocked (HS)
Detection (+) or no detection (−) of viable spores based on bacterial colony counts
Each sign (+ or −) represents results of one replication of the experiment
n/a = not applicable; no data collected.

TABLE 10

Influence of drying temperature and time on the spore viability of aerobic mesophilic bacteria in naturally contaminated corncob particles with 65% (w/w) added water

| Temperature of Drying | Prior heat-shock | Drying time at specified temperature | | | | |
|---|---|---|---|---|---|---|
| | | 20 min | 25 min | 30 min | 35 min | 40 min |
| 82° C. | NHS | +++ | +++ | +++ | +++ | +++ |
| | HS | +++ | +++ | +++ | +++ | +++ |
| 93° C. | NHS | +++ | +++ | +++ | +++ | +++ |
| | HS | +++ | +++ | +++ | +++ | +++ |
| 104° C. | NHS | +++ | +++ | +++ | +++ | +++ |
| | HS | +++ | +++ | +++ | +++ | +++ |
| 115° C. | NHS | +++ | +++ | +++ | +++ | +++ |
| | HS | +++ | +++ | +++ | +-- | --- |
| 121° C. | NHS | +++ | +++ | +++ | +++ | +++ |
| | HS | +++ | +++ | ++- | --- | --- |
| 176.6° C. | NHS | +++ | +++ | --- | --- | --- |
| | HS | +++ | +++ | n/a | n/a | n/a |
| | HS | --- | --- | n/a | n/a | n/a |

Non-heat-shocked (NHS) and heat-shocked (HS)
Detection (+) or no detection (−) of viable spores based on bacterial colony counts
Each sign (+ or −) represents results of one replication of the experiment
n/a = not applicable; no data collected.

Example 6: Evaluation of Final Moisture Content of Corncob Particles

In order to determine the effect of various heat-shock, tempering and heating treatment parameters on the moisture content of PFR material, corncob particles (⅛") were subjected to heating at 80° C. for 15 minutes to heat-shock naturally occurring bacterial spores. Prior to heat-shock treatment, the corncob particles were sprayed with filter-sterilized water to obtain initial amounts of added water of 40, 45, 50, 60, 70, 80 or 100% (w/w). After heat-shock, the particles were tempered at 40° C. for 30 minutes in a heater water bath set at 40° C. before drying them in a convection oven/dryer.

Duplicate fifty-gram portions of wet corncob particles that were exposed to heat-shock conditions for bacterial spores and tempered were then placed in separate sterile aluminum trays. The particles were heated in a forced-air convection oven/dryer at 115, 121, 150 or 155° C. for selected time periods ranging from 20 to 40 minutes. The heated particles were cooled at room temperature for 10 minutes in a laminar flow hood (23±1° C.) with the blower activated. One 50-g batch of corncob particles was aseptically divided into two 25-g portions and used for microbial analysis to determine numbers of viable aerobic mesophilic spores in the particles as described above. The remaining 50-g samples were used to determine their moisture content.

The corncob samples were weighed and the initial weight of each sample was recorded. The final moisture content of the particles was determined by drying them to a constant weight in a convection oven set at 155° C. and monitoring the change in weight at set time intervals (20, 25, 30, and 35 minutes). The particles were considered dried when the weight change between dryings was less than 0.5 gram. The dried samples were cooled at room temperature (22±1° C.) for 10 to 15 minutes in a laminar flow hood with the blower activated. The samples were weighed again and the amount of moisture lost was calculated by subtracting the final weight of a sample from its initial weight. The following equation was used to calculate the final percent moisture:

$$\text{Final percent (\%) moisture} = \frac{\text{weight of moisture lost (grams)}}{\text{Initial weight of corncob particles (grams)}} \times 100$$

Water activity (a measure of the amount of free or "unbound" moisture) of the corncob particles was measured using an Aqua Lab water activity meter. As a reference, a water activity value of 1.000 was obtained for distilled water.

Before they were dried to a constant weight, traditional corncob particles (⅛") had a water activity (aW) of 0.364. The moisture content and water activity of the corncob particles after being dried to a constant weight averaged 8.33% and 0.273, respectively. Final moisture content of the corncob particles decreased with increase in drying temperature and time.

Non-heat-shocked (NHS) bacterial spores were not destroyed by any of the temperature and time combinations used in the present study. Generally, increased amounts added moisture resulted in an increased sensitivity of the heat-shocked (HS) spores. For example, with increased amounts of added moisture, the heat-shocked spores were destroyed at shorter exposure times at drying temperatures of 115° C., 121° C. and 150° C.

There were no marked differences in the effect of 25 minutes or 30 minutes of tempering time on destruction of the spores; however, a tempering time of 45 minutes consistently resulted in increased destruction of the bacterial spores during drying of the corncob particles. This effect might be due to the fact that a "wave" of germination occurs in a spore population, and not all spores are at the same point in the germination process at a given time. Increasing the tempering time most likely increases the amount of germinating spores.

TABLE 11

Water activity of non-treated (control) corncob particles (⅛").

| Corncob particle sample no. | Sample weight (grams) | Water Activity (aw) |
|---|---|---|
| 1 | 1.00 | 0.364 |
| 2 | 1.01 | 0.363 |
| 3 | 1.00 | 0.363 |
| 4 | 1.03 | 0.365 |
| 5 | 1.00 | 0.363 |
| Average values | 1.01 | 0.364 |

TABLE 12

Moisture content and water activity ($a_W$) of non-treated corncob particles (⅛") as determined by drying particles to a constant weight in a laboratory scale convection oven set at 155° C.

| Corncob particle sample no | Initial Weight (grams) | Drying time (min) | Weight after drying (grams) | Weight of moisture lost (grams) | Calculated moisture content (%) | Water activity (aW) |
|---|---|---|---|---|---|---|
| Rep 1 | | | | | | |
| 1 | 50.13 | 20 | 45.98 | 4.15 | 8.28 | 0.284 |
| 2 | 50.05 | 25 | 45.90 | 4.13 | 8.26 | 0.281 |
| 3 | 50.16 | 30 | 45.98 | 4.18 | 8.34 | 0.278 |
| 4 | 50.02 | 35 | 45.86 | 4.16 | 8.33 | 0.273 |
| Rep 2 | | | | | | |
| 1 | 50.00 | 20 | 45.87 | 4.13 | 8.27 | 0.280 |
| 2 | 50.22 | 25 | 46.05 | 4.17 | 8.30 | 0.278 |
| 3 | 50.10 | 30 | 45.95 | 4.15 | 8.29 | 0.271 |
| 4 | 50.18 | 35 | 45.99 | 4.19 | 8.35 | 0.274 |
| Rep 3 | | | | | | |
| 1 | 50.04 | 20 | 45.93 | 4.11 | 8.22 | 0.282 |
| 2 | 50.02 | 25 | 45.88 | 4.14 | 8.28 | 0.280 |
| 3 | 50.12 | 30 | 45.96 | 4.16 | 8.30 | 0.275 |
| 4 | 50.19 | 35 | 45.92 | 4.17 | 8.32 | 0.270 |

Average moisture content = 8.33%
Average water activity = 0.272

TABLE 13

Effect of drying temperature and time on the moisture content (%) of corncob particles with 40% (w/w) added water.

| Temperature of Drying | Aerobic mesophilic spores | | 20 min | 25 min | 30 min | 35 min | 40 min |
|---|---|---|---|---|---|---|---|
| 115° C. | % Moisture Content | | 10.94 | 10.61 | 9.76 | 9.40 | 9.05 |
| | Viable spores | NHS | ++ | ++ | ++ | ++ | ++ |
| | | HS | ++ | ++ | ++ | ++ | −− |
| 121° C. | % Moisture Content | | 10.86 | 10.78 | 9.63 | 9.28 | 8.96 |
| | Viable spores | NHS | ++ | ++ | ++ | ++ | ++ |
| | | HS | ++ | ++ | ++ | −− | −− |
| 150° C. | % Moisture Content | | 9.34 | 8.75 | 8.28 | 7.92 | nd |
| | Viable spores | NHS | ++ | ++ | ++ | ++ | |
| | | HS | ++ | −− | −− | −− | |
| 155° C. | % Moisture Content | | 8.46 | 8.39 | 7.89 | 7.68 | nd |
| | Viable spores | NHS | ++ | ++ | ++ | ++ | |
| | | HS | −− | −− | −− | −− | |

Presence (+) or absence (−) of viable spores based on bacterial colony counts
nd = no data collected;
NHS = no heat shock;
HS = heat shock

TABLE 14

Effect of drying temperature and time on the moisture content (%) of corncob particles with 45% (w/w) added water.

| Temperature of Drying | Aerobic mesophilic spores | | 20 min | 25 min | 30 min | 35 min | 40 min |
|---|---|---|---|---|---|---|---|
| 115° C. | % Moisture Content | | 11.63 | 11.06 | 10.73 | 10.24 | 9.87 |
| | Viable spores | NHS | ++ | ++ | ++ | ++ | ++ |
| | | HS | ++ | ++ | ++ | −− | −− |
| 121° C. | % Moisture Content | | 11.30 | 10.84 | 10.47 | 9.88 | 9.65 |

TABLE 14-continued

Effect of drying temperature and time on the moisture content (%) of corncob particles with 45% (w/w) added water.

| Temperature of Drying | Aerobic mesophilic spores | | 20 min | 25 min | 30 min | 35 min | 40 min |
|---|---|---|---|---|---|---|---|
| | Viable spores | NHS | ++ | ++ | ++ | ++ | ++ |
| | | HS | ++ | ++ | ++ | -- | -- |
| 150° C. | % Moisture Content | | 9.26 | 8.91 | 8.55 | 8.30 | nd |
| | Viable spores | NHS | ++ | ++ | ++ | ++ | |
| | | HS | -- | -- | -- | -- | |
| 155° C. | % Moisture Content | | 8.84 | 8.22 | 8.00 | 7.89 | nd |
| | Viable spores | NHS | ++ | ++ | ++ | ++ | |
| | | HS | -- | -- | -- | -- | |

Presence (+) or absence (−) of viable spores based on bacterial colony counts
nd = no data collected;
NHS = no heat shock;
HS = heat shock

TABLE 15

Effect of drying temperature and time on the moisture content (%) of corncob particles with 50% (w/w) added water.

| Temperature of Drying | Aerobic mesophilic spores | | 20 min | 25 min | 30 min | 35 min | 40 min |
|---|---|---|---|---|---|---|---|
| 115° C. | % Moisture Content | | 11.85 | 11.28 | 10.94 | 10.46 | 10.12 |
| | Viable spores | NHS | ++ | ++ | ++ | ++ | ++ |
| | | HS | ++ | ++ | ++ | -- | -- |
| 121° C. | % Moisture Content | | 11.59 | 11.20 | 10.82 | 10.21 | |
| | Viable spores | NHS | ++ | ++ | ++ | ++ | ++ |
| | | HS | ++ | ++ | ++ | -- | -- |
| 150° C. | % Moisture Content | | 9.48 | 9.17 | 9.04 | 8.60 | nd |
| | Viable spores | NHS | ++ | ++ | ++ | ++ | |
| | | HS | -- | -- | -- | -- | |
| 155° C. | % Moisture Content | | 9.16 | 8.78 | 8.53 | 8.30 | nd |
| | Viable spores | NHS | ++ | ++ | ++ | ++ | |
| | | HS | -- | -- | -- | -- | |

Presence (+) or absence (−) of viable spores based on bacterial colony counts
nd = no data collected;
NHS = no heat shock;
HS = heat shock

TABLE 16

Effect of drying temperature and time on the moisture content (%) of corncob particles with 60% (w/w) added water.

| Temperature of Drying | Aerobic mesophilic spores | | 20 min | 25 min | 30 min | 35 min | 40 min |
|---|---|---|---|---|---|---|---|
| 115° C. | % Moisture Content | | 11.96 | 11.63 | 11.38 | 10.96 | 10.68 |
| | Viable spores | NHS | ++ | ++ | ++ | ++ | ++ |
| | | HS | ++ | ++ | +− | -- | -- |
| 121° C. | % Moisture Content | | 11.86 | 11.58 | 11.21 | 10.85 | |
| | Viable spores | NHS | ++ | ++ | ++ | ++ | ++ |
| | | HS | ++ | ++ | -- | -- | -- |
| 150° C. | % Moisture Content | | 10.85 | 10.72 | 10.25 | 9.76 | nd |
| | Viable spores | NHS | ++ | ++ | ++ | ++ | |
| | | HS | -- | -- | -- | -- | |
| 155° C. | % Moisture Content | | 10.69 | 10.38 | 9.87 | 9.43 | nd |
| | Viable spores | NHS | ++ | ++ | ++ | ++ | |
| | | HS | -- | -- | -- | -- | |

Presence (+) or absence (−) of viable spores based on bacterial colony counts
nd = no data collected;
NHS = no heat shock;
HS = heat shock

TABLE 17

Effect of drying temperature and time on the moisture content (%) of corncob particles 70% (w/w) added water.

| Temperature of Drying | Aerobic mesophilic spores | | 25 min | 30 min | 35 min | 40 min |
|---|---|---|---|---|---|---|
| 115° C. | % Moisture Content | | 12.28 | 12.01 | 11.73 | 11.40 |
| | Viable spores | NHS | ++ | ++ | ++ | ++ |
| | | HS | ++ | -- | -- | -- |
| 121° C. | % Moisture Content | | 12.01 | 11.68 | 11.33 | 11.97 |
| | Viable spores | NHS | ++ | ++ | ++ | ++ |
| | | HS | ++ | -- | -- | -- |
| 150° C. | % Moisture Content | | 11.42 | 11.14 | 10.82 | 10.48 |
| | Viable spores | NHS | ++ | ++ | ++ | ++ |
| | | HS | -- | -- | -- | -- |
| 155° C. | % Moisture Content | | 11.12 | 10.64 | 9.98 | 9.67 |
| | Viable spores | NHS | ++ | ++ | ++ | ++ |
| | | HS | -- | -- | -- | -- |

Presence (+) or absence (−) of viable spores based on bacterial colony counts;
NHS = no heat shock;
HS = heat shock

TABLE 18

Effect of drying temperature and time on the moisture content (%) of corncob particles with 80% (w/w) added water.

| Temperature of Drying | Aerobic mesophilic spores | | 25 min | 30 min | 35 min | 40 min |
|---|---|---|---|---|---|---|
| 115° C. | % Moisture Content | | 12.69 | 12.36 | 12.02 | 11.71 |
| | Viable spores | NHS | ++ | ++ | ++ | ++ |
| | | HS | ++ | -- | -- | -- |
| 121° C. | % Moisture Content | | 12.58 | 12.24 | 11.90 | 11.62 |
| | Viable spores | NHS | ++ | ++ | ++ | ++ |
| | | HS | ++ | -- | -- | -- |
| 150° C. | % Moisture Content | | 11.84 | 11.52 | 11.16 | 10.66 |
| | Viable spores | NHS | ++ | ++ | ++ | ++ |
| | | HS | -- | -- | -- | -- |
| 155° C. | % Moisture Content | | 11.26 | 10.82 | 10.21 | 9.88 |
| | Viable spores | NHS | ++ | ++ | ++ | ++ |
| | | HS | -- | -- | -- | -- |

Presence (+) or absence (−) of viable spores based on bacterial colony counts;
NHS = no heat shock;
HS = heat shock

TABLE 19

Effect of drying temperature and time on the moisture content (%) of corncob particles with 100% (w/w) added water.

| Temperature of Drying | Aerobic mesophilic spores | | 25 min | 30 min | 35 min | 40 min |
|---|---|---|---|---|---|---|
| 115° C. | % Moisture Content | | 12.82 | 12.58 | 12.26 | 11.93 |
| | Viable spores | NHS | ++ | ++ | ++ | ++ |
| | | HS | ++ | -- | -- | -- |

TABLE 19-continued

Effect of drying temperature and time on the moisture content (%) of corncob particles with 100% (w/w) added water.

| Temperature of Drying | Aerobic mesophilic spores | | 25 min | 30 min | 35 min | 40 min |
|---|---|---|---|---|---|---|
| 121° C. | % Moisture Content | | 12.80 | 12.47 | 12.02 | 11.86 |
| | Viable spores | NHS | ++ | ++ | ++ | ++ |
| | | HS | ++ | -- | -- | -- |
| 150° C. | % Moisture Content | | 11.98 | 11.69 | 11.27 | 10.85 |
| | Viable spores | NHS | ++ | ++ | ++ | ++ |
| | | HS | -- | -- | -- | -- |
| 155° C. | % Moisture Content | | 11.49 | 10.97 | 10.46 | 9.97 |
| | Viable spores | NHS | ++ | ++ | ++ | ++ |
| | | HS | -- | -- | -- | -- |

Presence (+) or absence (−) of viable spores based on bacterial colony counts;
NHS = no heat shock;
HS = heat shock Example 7: Optimizing the Thermal Destruction of Bacterial Spores in PFR Material Based on results of the above examples, applying this sporicidal treatment drastically reduced the numbers of viable bacterial spores in corncob particles (⅛") by ~10,000-fold (4.0-log). While substantial numbers of spores can be consistently destroyed by this process, on many occasions it was noticed that a small population of spores (about 3.0 to $8.0 \times 10^1$ spores/g) survived the process even at the highest thermal treatment applied (155° C. for 25 minutes). This observation was based on bacterial colonies that emerged on agar plates after 48 hours of incubation (at ~60 to 72 hours).

Although in standard methods of microbial analysis (for the aerobic plate count), 48 hours of incubation of inoculated agar plates are typically used, the emergence of bacterial colonies on agar plates after 48 hours, if noticed by the testing laboratory, can markedly impact the results reported. In this regard, reports on substantial numbers of bacterial survivors in the treated corncob particles can "weaken" claims that the particles are of very high microbial quality and result in loss of acceptance by animal research laboratories.

To address the possibility that some spores were not triggered to germinate by one heat shock, a number of modifications to the sanitization process were assessed in order to optimize destruction of bacterial spores in PFR material. One approach was to add a second heat shock treatment before final thermal treatment used for drying the particles to determine if this approach could further reduce the numbers of spore survivors.

A second approach was to evaluate differences in viability of types of bacterial spores (isolated from corncob particles) and exposed to heat-shock, tempering, and thermal treatment. Since most spores were being killed by the process, an additional hypothesis was heat resistance varied among spores present in the corncob particles. In this regard, we decided to test this latter hypothesis first before exploring the aspect of germination.

A third approach was to evaluate the effects of water with selected germinant solutions, or corn steep water, on the extent of spore germination in corncob particles. It is known that in addition to adequate moisture plus ideal ranges in heat-shock temperature and time, spores may need certain nutrients (germinants) to initiate germination. This led us to explore the use of several substances in the water used for moistening the corncob particles prior to heat-shock.

Influence of Two Heat-Shock and Tempering Cycles on Thermal Destruction of Bacterial Spores in Corncob Particles Traditional corncob particles (⅛") with 80% or 100% (w/w) added moisture were exposed to 80° C. for 15 minutes to heat-shock bacterial spores and kill bacterial vegetative cells. Before heat-shock treatment, the corncob particles were soaked with filter-sterilized water to obtain 80% or 100% (w/w) added moisture. After each heat-shock, the particles were tempered at 40° C. for 45 minutes. This process was repeated twice before drying the corncob particles in a convection oven/dryer. Corncob particles that were not heat-shocked but soaked with water and heated in a convection oven served as control.

Separate portions (25-g) of wet corncob particles: i) No heat-shock (NHS; control), ii) heat-shock/tempering once (HST1x), and iii) heat-shock/tempering twice (HST2x) were placed in separate sterile aluminum trays. All three sets of particles were dried by heating in a forced-air convection oven/dryer at 150 and 155° C.

During heating at a pre-determined temperature the particles were removed at set times (25, 30, 35, and 40 minutes), tempered to ~22±1° C. for 30 minutes in a laminar flow biological hood (with the fan on), then analyzed for numbers of viable bacterial spores based on colony counts of spore-forming bacteria.

Microbial analysis of corncob particles was performed using standard methods as described above. Inoculated DTA plates were incubated at 35° C. for 72 hours (for mesophilic aerobic spore-formers).

Two replications of each experiment were conducted with two corncob samples analyzed per treatment per replication. The average counts of viable microorganisms (transformed to $\log_{10}$ CFU/g) were recorded. For each replicate experiment, when bacterial survivors were detected, the average $\log_{10}$ CFU/g was used to represent numbers of viable spore forming bacteria. Because the detection limit was $1.0 \times 10^1$ CFU/g, the value of <10 was used when no bacterial colonies were detected on agar plates from the lowest dilution ($10^{-1}$) of the corncob samples.

The effect of one or two sequential heat-shock/tempering processes on the heat destruction of bacterial spores in corncob particles (⅛") with 80% (w/w) added water are shown in Table 20.

TABLE 20

Influence of one or two sequential heat-shock/tempering processes on the heat destruction of bacterial spores in corncob particles with 80% (w/w) added water.

| Drying Temperature | Heat-shock and tempering | 25 min | 30 min | 35 min | 40 min |
|---|---|---|---|---|---|
| Rep 1 | | | | | |
| 150° C. | NHS (control) | 4.13 | 3.63 | 3.18 | 2.79 |
| | HST1x | 1.78 | 1.48 | 1.30 | <1.0 |
| | HST2x | 1.60 | 1.54 | 1.00 | <1.0 |
| 155° C. | NHS (control) | 4.22 | 3.75 | 3.36 | nd |
| | HST1x | 1.74 | 1.30 | 1.00 | nd |
| | HST2x | 1.70 | 1.48 | 1.00 | nd |
| Rep 2 | | | | | |
| 150° C. | NHS (control) | 4.24 | 3.72 | 3.29 | 2.71 |
| | HST1x | 1.90 | 1.69 | 1.48 | 1.0 |
| | HST2x | 1.84 | 1.48 | 1.30 | <1.0 |

TABLE 20-continued

Influence of one or two sequential heat-shock/tempering processes on the heat destruction of bacterial spores in corncob particles with 80% (w/w) added water.

| Drying Temperature | Heat-shock and tempering | 25 min | 30 min | 35 min | 40 min |
|---|---|---|---|---|---|
| 155° C. | NHS (control) | 4.18 | 3.98 | 3.80 | nd |
|  | HST1x | 1.54 | 1.39 | 1.00 | nd |
|  | HST2x | 1.48 | 1.39 | 1.30 | nd |

Counts of viable bacterial spores are expressed as $\log_{10}$ CFU/g. Bacterial colonies were counted at 72 hours of incubation of agar plates
No heat-shock (NHS; control); one heat-shock/tempering (HST1x);
heat-shock/tempering twice (HST 2x);
n/a = not applicable;
nd = no data collected The initial numbers of viable spores in the corncob particles before application of the sporicidal process were ~5.20 $\log_{10}$ CFU/g based on results of microbial analysis of the particles just after heat-shock (80° C. for 15 minutes). The average number of viable bacterial spores in non-heat-shock (NHS) corncob particles (control) after 25 minutes of thermal treatment at 150° C. and 155° C. was 4.18 and 4.20 $\log_{10}$ CFU/g, respectively. These results represent decreases of only 1.02 and 1.0 $\log_{10}$ CFU/g reductions, respectively, in the initial numbers of viable spores in the corncob particles.

Heat-shock and tempering of corncob particles once (HST1x) or twice (HST2x) prior to drying resulted in drastic reductions in numbers of viable spores following thermal (drying) treatment at 150° C. and 155° C. (see Table 20). In corncob particles that received one prior heat-shock/tempering (HST1x), average reductions in numbers of viable spores compared to initial number of viable spores were 3.40, 3.65, and 3.85 $\log_{10}$ following thermal treatment at 150° C. for 25, 30, and 35 minutes, respectively. In comparison, corncob particles that received two prior heat-shock/tempering (HST2x) had an average reductions in initial numbers of viable spores of 3.52, 3.73, and 4.09 $\log_{10}$ following thermal treatment at 150° C. for 25, 30, and 35 minutes, respectively.

Figure 6A:
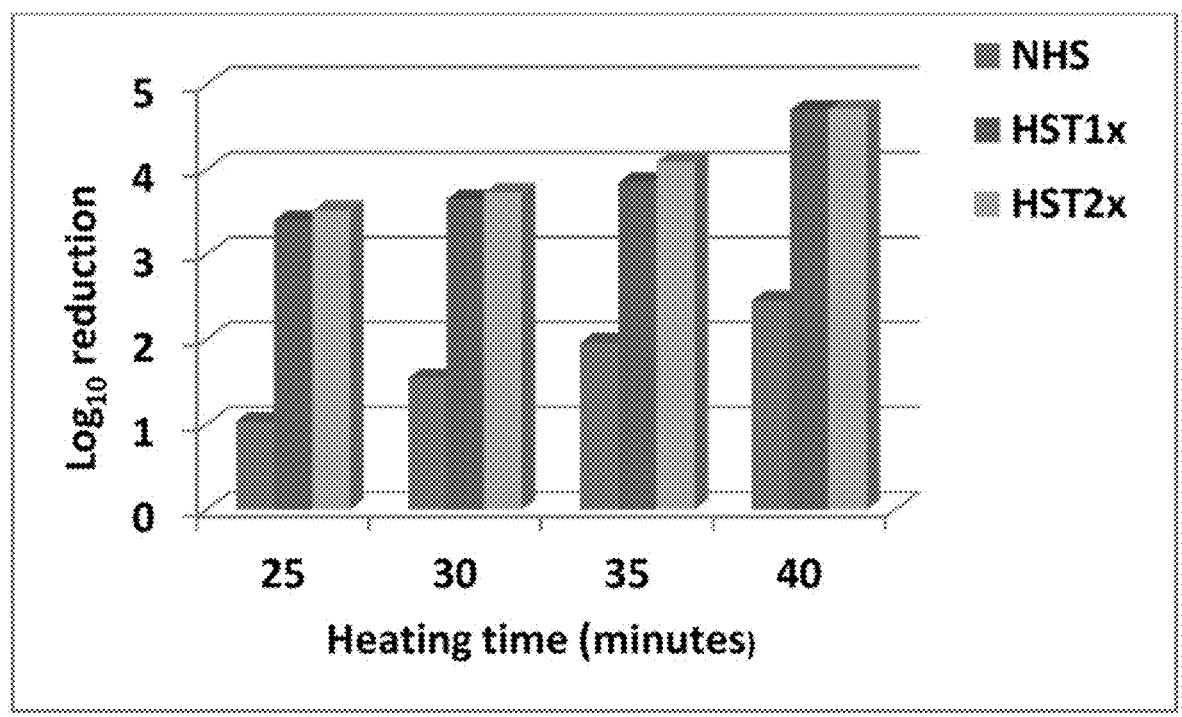
FIG. 6 (A-B) shows $\log_{10}$ CFU/g reductions in numbers of viable spores that were not heat shocked (NHS) or treated with HST1x or HST2x in corncob particles and heated at 150° C. for 25 to 40 minutes (A) or 155° C. for 25 to 35 minutes (B).
Figure 6B:
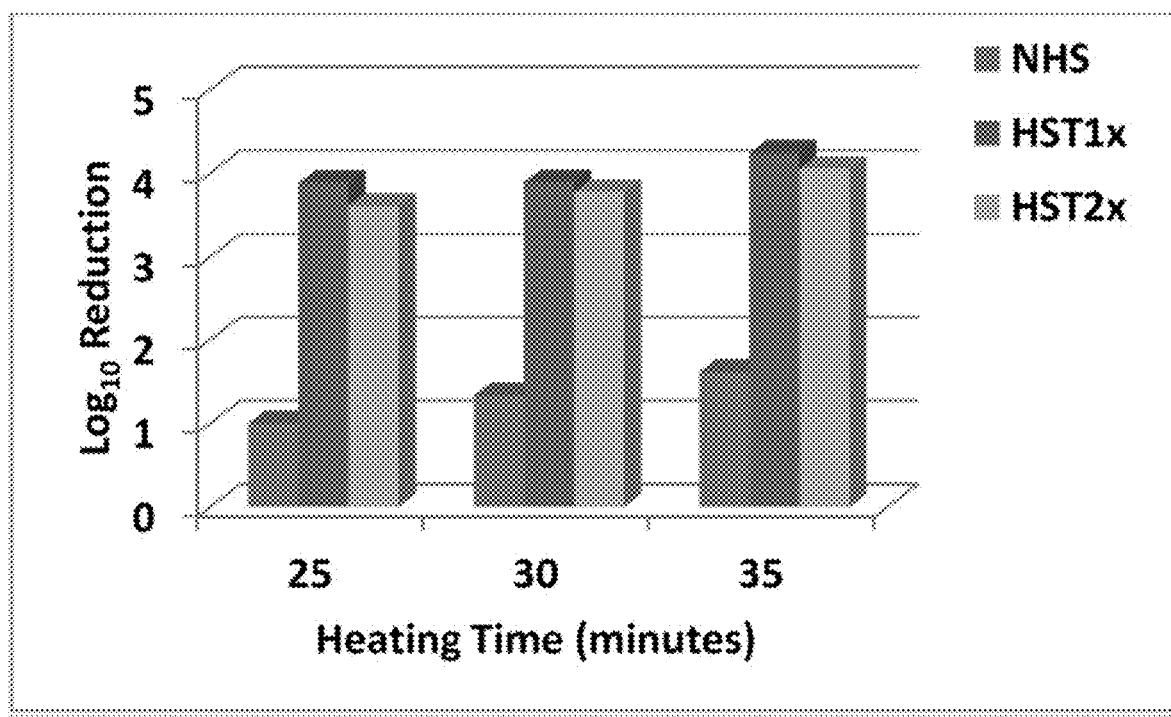

Average reductions in initial numbers of viable spores in corncob particles that received one prior heat-shock/tempering (HST1x) were 3.88, 3.89, and 4.24 $\log_{10}$, respectively, after 25, 30, and 35 minutes of thermal treatment at 155° C., compare to reductions of 3.61, 3.77, and 4.05 $\log_{10}$ in initial numbers of viable spores in corncob particles that received two prior heat-shock/tempering (HST2x). Differences in $\text{Log}_{10}$ reductions in numbers of viable spores that were not heat-shocked (NHS) or treated with HST1x or HST2x and heated at 150° C. and 155° C. are shown in FIGS. 6A and 6B, respectively.

Non-heat shocked spores exhibited very high heat resistance; $\log_{10}$ reductions in NHS spores following heating at 150° C. for 25, 30, 35 and 40 minutes were only 1.03, 1.54, 1.96, and 2.45, respectively (6A). $\log_{10}$ reductions in NHS spores following heating at 155° C. for 25, 30, and 35 minutes were 1.0, 1.33, and 1.62, respectively (FIG. 6B). There were very little differences in $\text{Log}_{10}$ reductions of numbers of viable spores treated with HST1x or HST2x and heated at 150° C.; differences were 0.12, 0.08, 0.25 and 0.50 $\text{Log}_{10}$ CFU/g, following heating of corncob particles for 25, 30, 35 and 40 minutes, respectively (FIG. 6A). Similar negligible differences were observed in $\text{Log}_{10}$ reductions of numbers of viable spores treated with HST1x or HST2x and heated at 155° C.; differences were 0.27, 0.12, and 0.19 $\text{Log}_{10}$ CFU/g, following heating of corncob particles for 25, 30, and 35 minutes, respectively (FIG. 6B).

Differences in Survival in Types of Bacterial Spores Isolated from Corncob Particles and Exposed to Heat-Shock, Tempering and Thermal Treatment Corncob particles (⅛") with 80% or 100% (w/w) added moisture were exposed to 80° C. for 15 minutes to heat-shock bacterial spores and kill bacterial vegetative cells. The heat-shocked particles were then analyzed for viable spores by plating samples of diluent (used to remove spores from the particles) on dextrose tryptone agar (DTA). The inoculated DTA plates were incubated at 35° C. for 72 hours before checking for different types of bacterial colonies.

Figure 7:
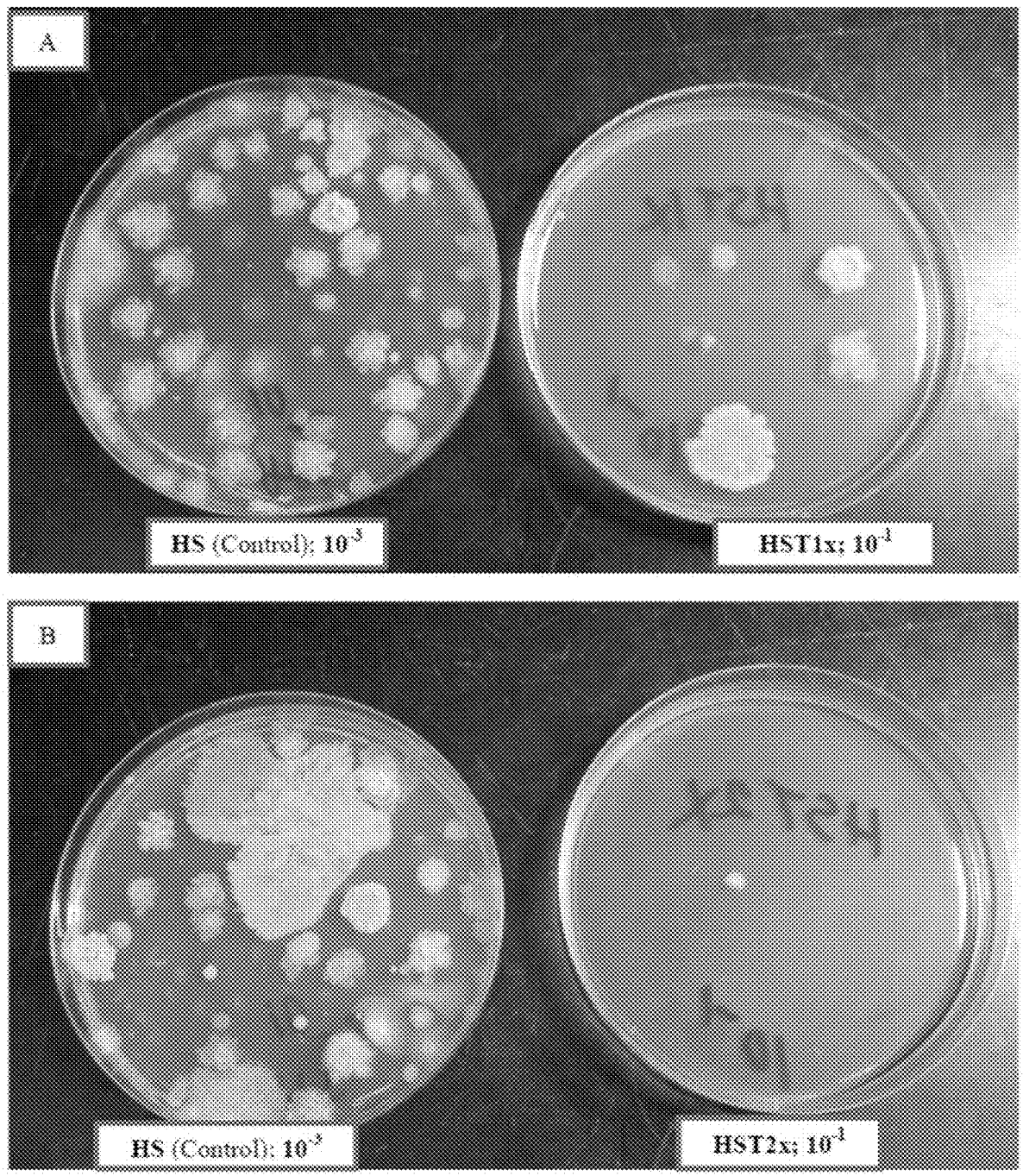
FIG. 7 (A-B) shows bacterial colonies from spores after thermal treatment (155° C., 25 min) of moist corncob particles (⅛"; 80% (w/w) added water) after heat shock (80° C., 15 min) and tempering at 40° C. for 45 minutes. (A) One heat shock/tempering process (HST1x) before thermal treatment; (B) Two sequential shock/tempering processes (HST2x) before thermal treatment.

Four types of bacterial colonies (called Isolates A, B, C, and D; see FIG. 7) were selected based on colony morphology (round, irregular, smooth, wrinkled, moist, dry). Each colony was streak plated on DTA. Following incubation of DTA plates, isolated colonies were picked and streak plated again on fresh DTA plates to ensure isolation of pure cultures. The final isolates were suspended in separate tubes of sterile 0.1% (w/v) peptone. Aliquots (0.2-ml) of each cell suspension were surface plated on DTA plates to produce a lawn of cells following incubation of the inoculated DTA plates at 35° C. or 55° C. for 72 hours. The DTA plates were held at 35° C. for a total of 7 days to induce formation of bacterial spores.

Bacterial spores were collected from the lawn of bacterial growth by pipetting 5.0 ml of sterile saline onto the surface of the lawn on each DTA plate an gently rubbing that surface with a sterile bent glass rod. The spores were harvested by centrifugation (10,000×g, 10 min, 4° C.) of the spore suspensions and discarding the supernatant. The pelleted spores were washed by suspending them in fresh saline by vortexing. The spore suspensions were subjected to centrifugation and their supernatants discarded. The pelleted spores were suspended in sterile saline. A portion of each spore suspension was subjected to heat-shock and then diluted and plated in DTA to determine the numbers of viable spores from each of the four types of bacterial colonies isolated from the corncob particles. This information was used to adjust the concentration of each spore suspension to obtain ~$10^7$ CFU/ml.

Samples (25-gram) of sterile corncob particles in sterile Erlenmeyer flasks were inoculated with suspensions of bacterial spores to obtain ~$10^5$ CFU/g. In each flask the inoculated particles were soaked with filter-sterilized water, heat-shocked, tempered and heat-treated as previously described above (HST1x).

Microbial analysis of corncob particles were analyzed using standard methods as described above. Inoculated DTA plates were incubated at 35° C. for 72 hours (for mesophilic aerobic spore-formers) and 55° C. for 72 hours (for thermophilic aerobic spore-formers).

Figure 8:
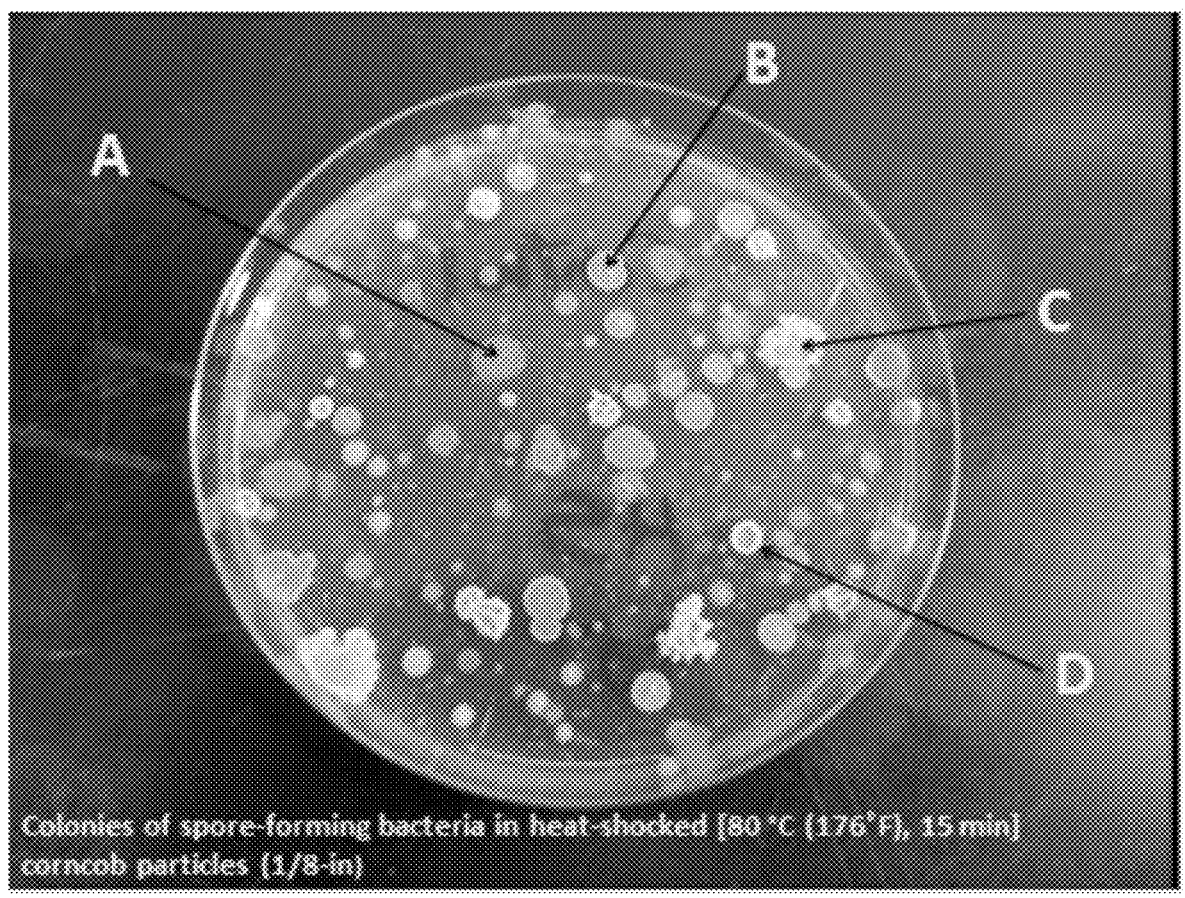
FIG. 8 shows colonies of bacterial sporeformers on dextrose tryptone agar following incubation at 35° C. for 72 hours.
Figure 9A:
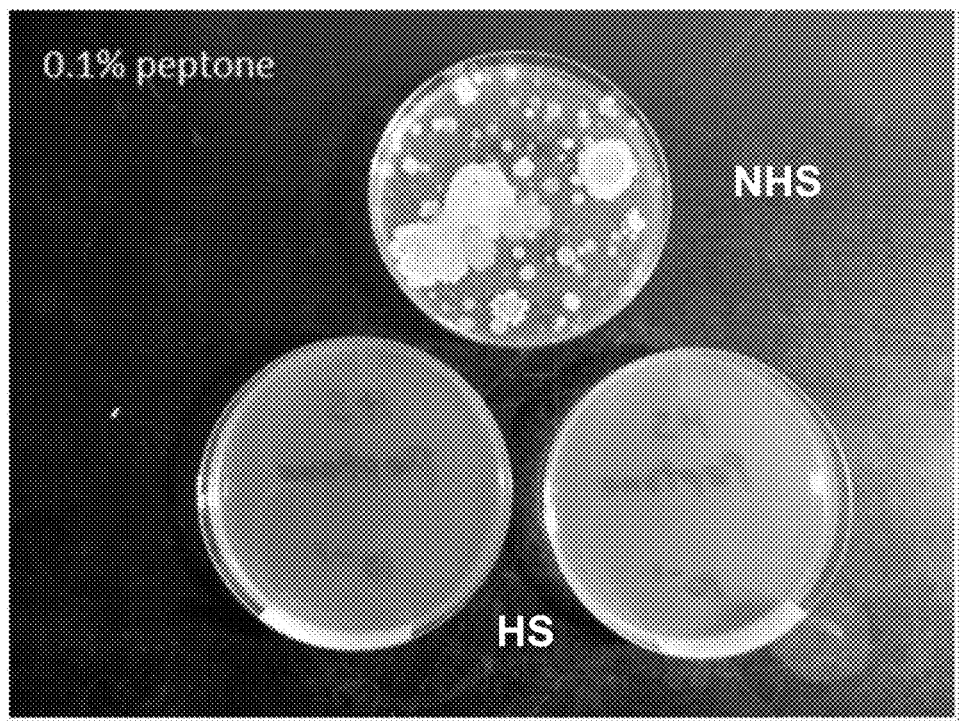
FIG. 9 (A-D) shows bacterial growth from non-heat shock (NHS; top plate in A-C, Control (no heating) in D) and heat shocked corncob particles (HS; bottom two plates in A-C, water, 0.25% corn steep water and 0.1% peptone in D). Corncob particles were coated with water containing the indicated germinate prior to heat shock, and all corncob particles were dried by heating at 155° C. for 25 minutes.
Figure 9B:
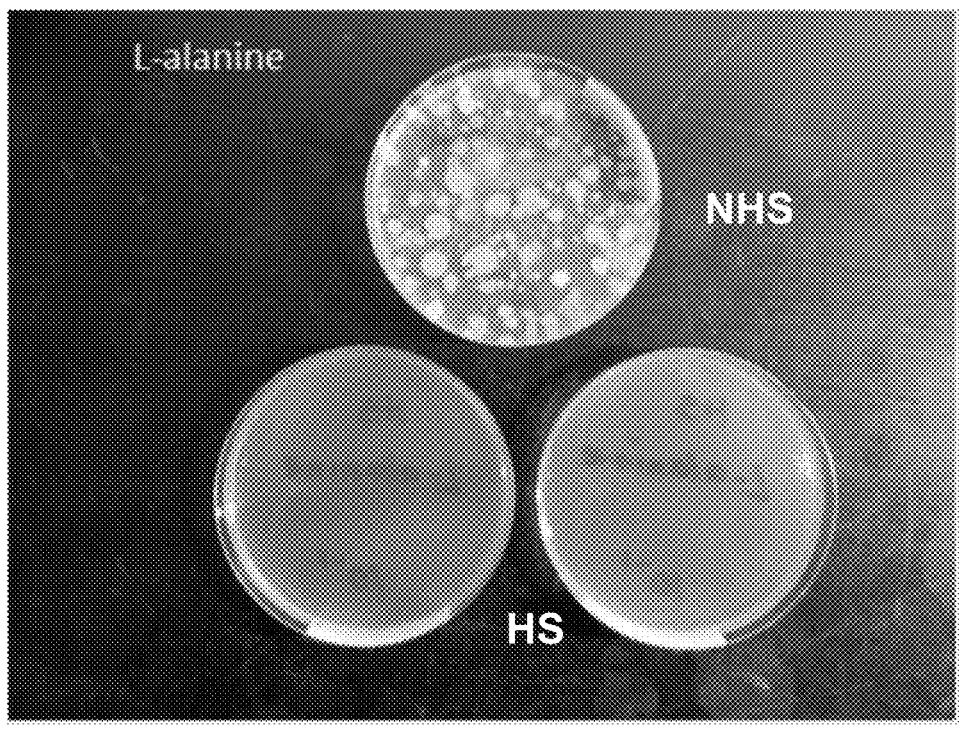
Figure 9C:
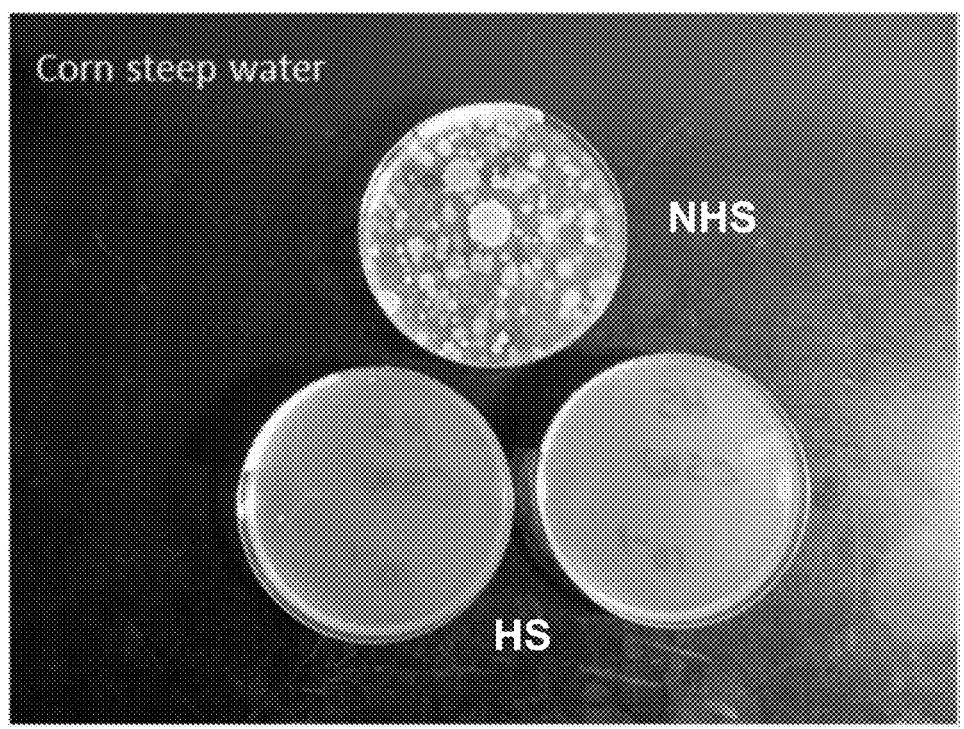
Figure 9D:
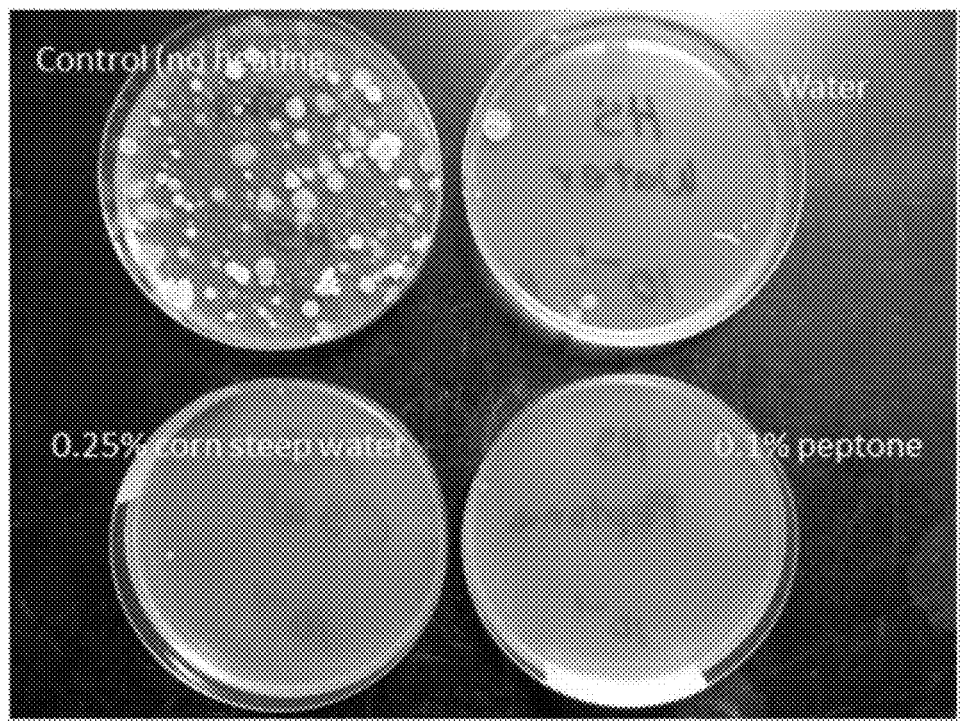

FIG. 8 shows colonies of bacterial spore-formers on DTA following incubation at 35° C. for 72 hours. Colonies that were selected and designated as Isolates A, B, C, and D are shown in the figure. Isolate A was a smooth watery colony, whereas, other isolates were generally wrinkled and dry. One of the spore-forming bacteria (Isolate A) from the corncob particles grew at both incubation temperatures 35° C. and 55° C. The other three isolates (B, C, and D) grew only at 35° C. Generally Isolate A exhibited a consistently higher resistance to the treatment compared to other isolates; however, there were no substantial differences in heat resistance among isolates (Table 21).

TABLE 21

Influence of heat-shock/tempering processes on the heat destruction of bacterial spores (Isolates A, B, C, and D) in corncob particles (⅛") with 80% (w/w) added water.

| Spore Isolate | Heat-shock and tempering | 25 min | 30 min | 35 min | 40 min |
|---|---|---|---|---|---|
| 150° C. final heating | | Survivors (log10 cfu/g) | | | |
| A | NHS (control) | 4.21 | 3.48 | 3.22 | 2.45 |
|   | HST1x | 1.86 | 1.72 | 1.46 | 1.04 |
| B | NHS (control) | 4.06 | 3.32 | 2.94 | 1.60 |
|   | HST1x | 1.64 | 1.48 | 1.00 | <1.0 |
| C | NHS (control) | 3.98 | 3.20 | 2.88 | 1.79 |
|   | HST1x | 1.66 | 1.53 | 1.30 | <1.0 |
| D | NHS (control) | 4.02 | 3.28 | 2.85 | 2.0 |
|   | HST1x | 1.78 | 1.60 | 1.47 | 1.0 |
| 155° C. final heating | | Survivors (log10 cfu/g) | | | |
| A | NHS (control) | 4.26 | 3.52 | 3.30 | |
|   | HST1x | 1.73 | 1.64 | 1.29 | |
| B | NHS (control) | 4.00 | 3.28 | 2.76 | |
|   | HST1x | 1.72 | 1.50 | 1.30 | |
| C | NHS (control) | 4.02 | 3.16 | 2.54 | |
|   | HST1x | 1.54 | 1.36 | 1.00 | |
| D | NHS (control) | 4.14 | 3.08 | 2.44 | |
|   | HST1x | 1.60 | 1.48 | 1.36 | |

Bacterial colonies were counted at 72 hours of incubation of agar plates.

Effect of Water and Selected "Germinant" Solutions on the Extent of Spore Germination in Corncob Particles The methods for application of the processing treatment (HST1x) were the same as previously described except that germinants were added to the water used for moistening the particles prior to treatment. Corn steep water was prepared by soaking cornmeal for one hour in water before use.

A summary of the results of three experiments are shown in Table 22 below. Only combinations of heat-shock and L-alanine, 0.1% peptone or 0.25% corn steep water were highly effective in achieving high levels of germination (i.e. as high as 98 and 99%).

TABLE 22

Effect of various germinants on bacterial spore germination in corncob particles.

| Treatment | Percent Germination |
|---|---|
| No heat-shock, no germinant | 5% |
| No heat-shock + L-alanine | 76% |
| Heat-shock + water | 11% |
| Heat-shock + L-alanine | 98% |
| Heat-shock + peptone (0.1%) | 99% |
| Heat-shock + corn steep water (0.25%) | 98% |

All heat-shocked particles were tempered at 40° C. for 15 minutes.

When L-alanine, 0.1% peptone or 0.25% corn steep water was used in the treatment process, final heating of the corncob particles at 150° C. or 155° C. was most effective in consistently reducing the population of bacterial spores to less than 10 CFU/g after 30 or 35 minutes of heating with only one heat-shock. (See FIG. 9).

Based on the results of these examples, a process for thermal destruction of microbes in PFR material has been developed. The sanitizing process subjects microbes, and in particular bacterial spores, in PFR material to conditions where they become sensitive to heating as they germinate and emerge as easily destroyed vegetative cells. The process steps include:

1. Activation by heat-shock, which prepares spores for germination. PFR material is completely coated with germinant enriched water. The germination of bacterial spores is further activated by increasing the temperature so that each particle is subjected to 80° C. for 15 minutes.
2. Germination and outgrowth of the spores by tempering at 40° C. for about 30-60 minutes. In this step of the process, spores are germinating or exhibiting outgrowth (producing vegetative cells) and become sensitive to heat. Generally the microbial enzymes involved in germination of bacterial spores work best within a temperature range of 35° C. to 42° C. A holding time of 40 minutes (minimum) is recommended for consistency of results because not all spores initiate the process of germination at the same time.
3. Destruction of vegetative cells by drying the PFR material via subjecting it to 150°-155° C. temperatures until the moisture level is 20% or below, preferably 10% or below (water activity level ($a_w$) of approximately 0.368).

Although specific embodiments of the invention have been described herein in some detail, all such descriptions are solely for the purposes of explaining the various aspects of the invention, and are not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A bedding material composition, produced by the process comprising:
   combining a PFR material with a germinant and water to produce a PFR material mix, wherein said germinant is effective to promote germination of bacterial endospores;
   exposing said PFR material mix to a heat-shock comprising 65° to 90° C. for 10 to 30 minutes;
   incubating the PFR material mix at between about 35° and about 45° C. for 20 to 35 minutes; and
   heating the PFR material mix at between 115 and 177° C. for approximately 15 to 40 minutes;
   wherein the PFR material mix contains 10 or less CFU/g of viable microbes in the PFR material; and
   wherein said PFR material mix contains less than 20% moisture content after said heating step.

2. The bedding material produced by the process according to claim 1, wherein said water and said germinant are added simultaneously.

3. The bedding material produced by the process according to claim 1, wherein said water and said germinant are added sequentially.

4. The bedding material composition produced by the process according to claim 1, wherein said heating step comprises heating said PFR material mix at between about 121° and 155° C.

5. The bedding material composition of claim 1, wherein said bedding material comprises one or more of pressed wood pellets, wood shavings, recycled cardboard, kenaf, sawdust, wheat straw, barley straw, oat straw, timothy straw, forage straws, and corncob particles.

6. The bedding material composition of claim 5, wherein said bedding material is corncob particles.

7. The bedding material composition of claim 1, wherein said process is performed in one day or less.

8. The bedding material composition of claim 7, wherein said process is performed in 5 hours or less.

9. The bedding material composition of claim 1, wherein said process further comprises adding a germinant to the PFR material prior to heat-shocking, wherein said germinant is effective in promotion of germination of bacterial endospores.

10. The bedding material composition produced by the process of claim 9, wherein said germinant is corn powder in aqueous solution.

11. The bedding material composition produced by the process according to claim 1, wherein said heating is performed in a forced-air convection oven/dryer.

12. The bedding material composition produced by the process according to claim 1, wherein said combining step comprises adding a liquid to the PFR material, wherein said amount is between about 40% and about 300% of the weight of said PFR material, and wherein said liquid is water.

13. The bedding material composition produced by the process according to claim 12, wherein said liquid comprises water that has been enriched with a germinant.

14. The bedding material composition produced by the process according to claim 13 wherein said liquid is enriched with 0.25% (w/w) corn powder.

15. The bedding material composition produced by the process according to claim 1 wherein said heat-shock is about 80° C. for about 15 minutes.

16. The bedding material composition produced by the process according to claim 1, further comprising holding the PFR material mix following said heat-shocking, wherein said holding comprises incubating the PFR material mix at between about 35° and about 55° C. for 10 to 30 minutes.

17. The method of claim 16, wherein the PFR material mix maintains an internal temperature of about 40° C. for at least 20 minutes.

18. The bedding material composition of claim 1 wherein said PFR material mix contains less than 10% moisture content after said heating.

19. A PFR material produced by the method comprising:
wetting the PFR material with water and a germinant, wherein PFR material is completely coated with said water and germinant and wherein said germinant is effective to promote germination of bacterial endospores;
exposing said PFR material to a heat-shock comprising 65° to 90° C. for 10 to 30 minutes;
incubating the PFR material at between about 35° and about 45° C. for 20 to 35 minutes; and
heating the PFR material at least between 115 and 177° C. for approximately 15 to 40 minutes;
wherein said process is performed in one day or less; and
wherein the PFR material contains 10 or less CFU/g of viable microbes in the PFR material; and
wherein said PFR material contains less than 20% moisture content after said heating.

20. The bedding material composition of claim 19 wherein said PFR material is an animal bedding material.

21. The bedding material composition of claim of claim 20 wherein said animal bedding material comprises corncob particles.

* * * * *